(12) United States Patent
Smith et al.

(10) Patent No.: US 10,092,483 B2
(45) Date of Patent: Oct. 9, 2018

(54) ARRAY OF ABSORBENT ARTICLES INCLUDING A FRAGRANCE ACCORD AND A LOTION COMPOSITION

(71) Applicant: The Procter & Gamble Company, Cincinnati, OH (US)

(72) Inventors: Alizha V. Smith, Wyoming, OH (US); Randall Glenn Marsh, Hamilton, OH (US); Oliver Edwin Clarke Mason, Mason, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 92 days.

(21) Appl. No.: 15/159,875

(22) Filed: May 20, 2016

(65) Prior Publication Data

US 2017/0202753 A1 Jul. 20, 2017

Related U.S. Application Data

(60) Provisional application No. 62/279,053, filed on Jan. 15, 2016, provisional application No. 62/181,791, filed on Jun. 19, 2015.

(51) Int. Cl.
*A61K 8/02* (2006.01)
*A61Q 19/00* (2006.01)
*A61L 15/46* (2006.01)

(52) U.S. Cl.
CPC ............ *A61K 8/0208* (2013.01); *A61L 15/46* (2013.01); *A61Q 19/00* (2013.01); *A61K 2800/88* (2013.01)

(58) Field of Classification Search
CPC .................................................. A61K 8/0208
See application file for complete search history.

(56) References Cited

U.S. PATENT DOCUMENTS

| | | |
|---|---|---|
| 5,143,679 A | 9/1992 | Weber et al. |
| 5,518,801 A | 5/1996 | Chappell et al. |
| 5,628,097 A | 5/1997 | Benson et al. |
| 5,658,639 A | 8/1997 | Curro et al. |
| 5,914,084 A | 6/1999 | Benson et al. |

(Continued)

OTHER PUBLICATIONS

13882 PCT International Search Report dated Sep. 8, 2016, 12 pages.

*Primary Examiner* — Arrie L Reuther
(74) *Attorney, Agent, or Firm* — James T. Fondriest; Sarah M. DeCristofaro

(57) ABSTRACT

An array of at least two commonly-branded absorbent articles, such as wipes products. The array includes a first wipes product and a second wipes product. Each wipes product may appeal to a different type of consumer, such as a light experience seeking consumer and a heavy experience seeking consumer. The first wipes product may include a first supply of wipes formed from a first substrate. The first supply of wipes is moistened with a first functional lotion composition including a first fragrance accord and a first lotion formula. The second wipes product may include a second supply of wipes formed from a second substrate. The second supply of wipes is moistened with a second functional lotion composition including a second fragrance accord and a second lotion formula. The second fragrance accord is different from the first fragrance accord, and the second lotion formula is different from the first lotion formula.

10 Claims, 5 Drawing Sheets

(56) References Cited

U.S. PATENT DOCUMENTS

| | | |
|---|---|---|
| 5,916,661 A | 6/1999 | Benson et al. |
| 6,114,263 A | 9/2000 | Benson et al. |
| 6,129,801 A | 10/2000 | Benson et al. |
| 6,383,431 B1 | 5/2002 | Dobrin et al. |
| 6,778,403 B2 | 8/2004 | Takenaka et al. |
| 7,005,557 B2 | 2/2006 | Klofta et al. |
| 7,037,569 B2 | 5/2006 | Curro et al. |
| 7,410,683 B2 | 8/2008 | Curro et al. |
| 7,553,532 B2 | 6/2009 | Turner et al. |
| 7,666,827 B2 | 2/2010 | Marsh et al. |
| 8,221,774 B2 | 7/2012 | Marsh et al. |
| 2004/0047136 A1 | 3/2004 | Takenaka et al. |
| 2004/0131820 A1 | 7/2004 | Turner et al. |
| 2004/0265534 A1 | 12/2004 | Curro et al. |
| 2005/0008680 A1 | 1/2005 | Deckner et al. |
| 2005/0008681 A1 | 1/2005 | Deckner et al. |
| 2011/0159074 A1 | 6/2011 | Warren et al. |
| 2011/0244199 A1 | 10/2011 | Brennan et al. |
| 2011/0268777 A1 | 11/2011 | Marsh et al. |
| 2012/0066852 A1 | 3/2012 | Trinkaus et al. |
| 2014/0208531 A1 | 7/2014 | Marsh et al. |
| 2014/0352090 A1* | 12/2014 | Schuchter ............ A61K 8/0208 15/104.93 |
| 2015/0017218 A1 | 1/2015 | Pettigrew et al. |
| 2015/0086659 A1 | 3/2015 | Klofta et al. |

* cited by examiner

US 10,092,483 B2

ARRAY OF ABSORBENT ARTICLES INCLUDING A FRAGRANCE ACCORD AND A LOTION COMPOSITION

CROSS REFERENCE TO RELATED APPLICATIONS

This application claims the benefit of U.S. Provisional Application No. 62/279,053 filed on Jan. 15, 2016, which claims the benefit of U.S. Provisional Application No. 62/181,791 filed on Jun. 19, 2015, which is incorporated herein by reference.

FIELD

The present disclosure relates to absorbent articles, and, more particularly, to absorbent articles including a functional lotion composition including various fragrance accords and lotion formulas.

BACKGROUND

Absorbent articles, such as wet wipes, may include fragrances. For some consumers, the perception of efficacy of an absorbent article in terms of cleaning and the ability to maintain and/or improve skin health may be affected by the scent or lack thereof of the absorbent article. Additionally, the scent of the absorbent article may affect the overall experience for a consumer. Different consumers perceive fragrance differently. For example, some consumers perceive a scented wipe that is able to provide a scent over the scent of a soil such as urine or feces as being able to clean well. This same type of consumer may also perceive a scented wipe that leaves a scent on the skin of a baby and/or the consumer as being able to clean well. However, other consumers may negatively perceive a wipe that leaves a long-lasting scent on the skin and/or a higher level of scent. This type of consumer may perceive a wipe having a relatively low level of scent as being able to clean better than a wipe having no scent.

Absorbent articles, such as wet wipes, may also include lotion compositions. For some consumers, the perception of efficacy of an absorbent article in terms of cleaning and the ability to maintain and/or improve skin health may be affected by the lotion composition added to the absorbent article or lack thereof. Additionally, the lotion composition present on the absorbent article may affect the overall diaper changing experience for a consumer. Similar to the above, different consumers prefer different lotion compositions. For example, some consumers perceive an absorbent article with a lotion composition that has a lubricious and creamy-feel as being able to clean well and/or as being able to offer skin conditioning and/or to offer skin protection. This same type of consumer may also perceive an absorbent article with a lotion composition that leaves a residue on the skin as being able to clean well. By contrast, other consumers may perceive an absorbent article that leaves a residue on the skin of the baby and/or the consumer negatively. This same type of consumer may perceive an absorbent article having a lotion composition that is lightweight and watery as being able to clean better than an absorbent article having a lotion composition that is perceived to be creamy-feeling and lubricous.

Further to the above, it is believed that consumers who perceive an absorbent article, such as a wipe, having a scent that may leave a lingering scent on the skin as being able to clean well also prefer an absorbent article, such as a wipe, that has a lotion composition that is creamy-feeling and lubricious and that may leave a residue on the skin. It is also believed that consumers who perceive a wipe having a relatively low level of scent during use and little or no scent that lingers on the skin as being able to clean better also prefer a lotion composition that is perceived as watery and lightweight. However, currently marketed wipes do not provide the aforementioned combinations. Thus, for example, consumers may only choose between absorbent articles that have a desired scent or a desired lotion composition.

Therefore, it would be beneficial to provide absorbent articles with a variety of fragrance compositions in combination with a variety of lotion compositions that meet the needs of various consumers.

SUMMARY

The present disclosure relates to an array of absorbent articles. In some embodiments, an array of at least two commonly-branded wipes products includes a first wipes product and a second wipes product. The first wipes product may include a first supply of wipes formed from a first substrate. The first supply of wipes may be moistened with a first functional lotion composition. The first functional lotion composition may include a first fragrance accord and a first lotion formula. The second wipes product may include a second supply of wipes formed from a second substrate. The second supply of wipes may be moistened with a second functional lotion composition. The second functional lotion composition may include a second fragrance accord and a second lotion formula. The second fragrance accord may be different from the first fragrance accord, and the second lotion formula may be different from the first lotion formula.

In some embodiments, an array of at least two commonly-branded absorbent articles includes a first absorbent article formed from a first substrate and a second absorbent article formed from a second substrate. The first absorbent article may be moistened with a first functional lotion composition. The first functional lotion composition may include a first fragrance accord and a first lotion formula. The first fragrance accord includes: from about 10% to about 15%, by total weight, of a perfume raw material having a vapor pressure of greater than 0.08 Torr at 25° C.; from about 35% to about 65%, by total weight, of a perfume raw material having a vapor pressure from 0.006 Torr at 25° C. to 0.08 Torr at 25° C.; and from about 20% to about 30%, by total weight, of a perfume raw material having a vapor pressure of less than 0.006 Torr at 25° C. The first lotion formula includes a first peak viscosity and a first average peak dynamic frictional force. The second absorbent article may be moistened with a second functional lotion composition. The second functional lotion composition includes a second fragrance accord and a second lotion formula. The second fragrance accord includes: from about 10% to about 20%, by total weight, of a perfume raw material having a vapor pressure of greater than 0.08 Torr at 25° C.; from about 20% to about 30%, by total weight, of a perfume raw material having a vapor pressure from 0.006 Torr at 25° C. to 0.08 Torr at 25° C.; and from about 45% to about 70%, by total weight, of a perfume raw material having a vapor pressure of less than 0.006 Torr at 25° C. The second lotion formula includes a second peak viscosity and a second average peak dynamic frictional force. The first peak viscosity of the first absorbent article may be less than the second peak viscosity of the second absorbent article, and the first average peak dynamic frictional force of the first absorbent article may be greater than the second average peak dynamic frictional force of the second absorbent article.

In some embodiments, an array of at least two commonly-branded absorbent articles includes a first absorbent article and a second absorbent article. The first absorbent article is formed from a first substrate. The first absorbent article may be moistened with a first functional lotion composition. The first functional lotion composition includes a first fragrance accord and a first lotion formula. The first fragrance accord includes: from about 10% to about 15%, by total weight, of a perfume raw material having a Kovats Index of less than 1300; from about 35% to about 65%, by total weight, of a perfume raw material having a Kovats Index from 1300 to 1450; and from about 20% to about 30%, by total weight, of a perfume raw material having a Kovats Index of greater than 1450. The first lotion formula includes a first peak viscosity and a first average peak dynamic frictional force. The second absorbent article is formed from a second substrate. The second absorbent article may be moistened with a second functional lotion composition. The second functional lotion composition may include a second fragrance accord. The second fragrance accord includes: from about 10% to about 20%, by total weight, of a perfume raw material having a Kovats Index of less than 1300; from about 20% to about 30%, by total weight, of a perfume raw material having a Kovats Index from 1300 to 1450; and from about 45% to about 70%, by total weight, of a perfume raw material having a Kovats Index of greater than 1450. The second lotion formula includes a second peak viscosity and a second average peak dynamic frictional force. The first peak viscosity of the first absorbent article may be less than the second peak viscosity of the second absorbent article, and the first average peak dynamic frictional force of the first absorbent article may be greater than the second average peak dynamic frictional force of the second absorbent article.

DETAILED DESCRIPTION

Figure 1:
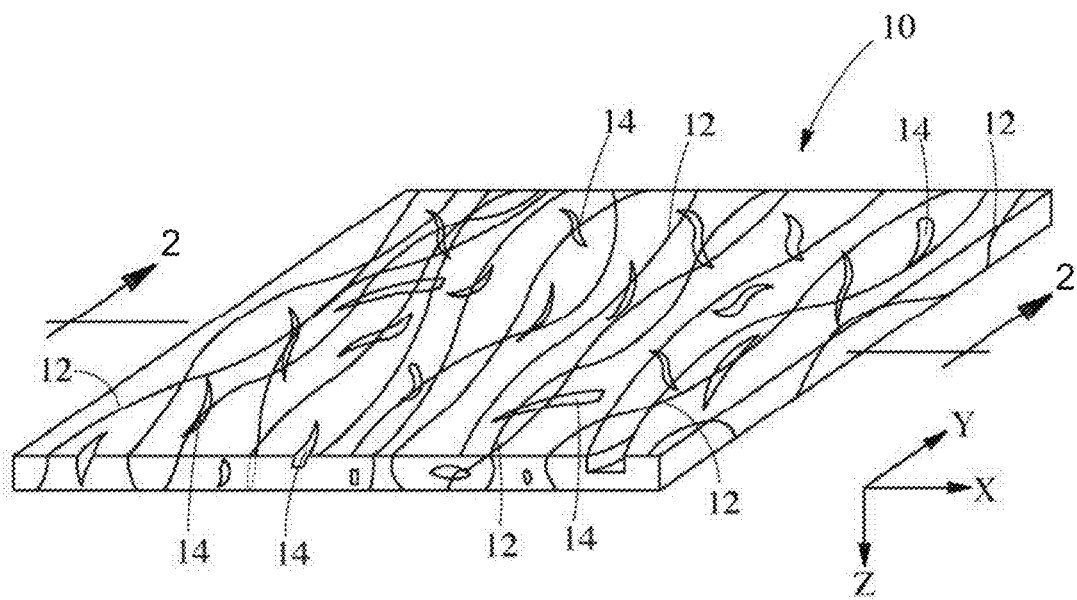
FIG. 1 is a schematic, perspective view of a substrate in accordance with one non-limiting embodiment of the present disclosure.

The following definitions may be useful in understanding the present disclosure:

"Soil" refers herein to matter that is extraneous to a surface being cleaned. For example, soils include body exudates, household matter, and outdoor matter. Body exudates include feces, menses, urine, vomitus, mucus, and the like. Household matter includes food, beverages, combinations thereof, and the like. Outdoor matter includes dirt, mud, snow, paint, crayons, and the like.

The term "disposable" is used herein to describe absorbent articles which generally are not intended to be laundered or otherwise restored or reused as an absorbent article (e.g., they are intended to be discarded after a single use and may also be configured to be recycled, composted or otherwise disposed of in an environmentally compatible manner).

"Array of absorbent articles" as used herein means a group of absorbent articles that provide a consumer benefit. An array of absorbent articles may include two or more products, such as wipes, diapers, incontinence products, and sanitary tissue products, that are simultaneously available for retail purchase. For example, a first wipe product and a second wipe product may be offered at the same retail location for purchase.

"Commonly-branded" as used herein means two or more absorbent articles that include the same brand name. A brand name is a word(s) and/or symbol(s) that communicate a single source identifier. A brand name identifies an absorbent article and/or service as exclusively coming from a single commercial source, such as a company. For example, a wet wipe may be sold under the brand name PAMPERS, which is also a trademark. The absorbent articles of the present disclosure may be marketed and/or packaged under a common brand name (i.e., the same brand name, such as PAMPERS).

"Commonly-sourced" as used herein means that two or more products are distributed by or distributed on behalf of a common source. For example, a first wipe with the brand name LUVS and a second wipes product with the brand name PAMPERS may be distributed by or distributed on behalf of the same company, such as The Procter & Gamble Company.

As used herein, percentages of the components of a lotion composition are given as the ratio of the weight of the component to the total weight of the lotion composition, unless otherwise indicated. Percentages reflect 100% active component material. For example, if a component is available in a dispersion at a concentration of 50% component to dispersion, by total weight, twice as much of the dispersion, by total weight, would be added to the lotion composition to provide the equivalent of 100% active component.

"Fragrance accord" refers to a mixture of two or more fragrance raw materials. The mixture may be formed prior to being disposed on an absorbent article, or two or more fragrance raw materials each may be disposed on an absorbent article.

"Neat" refers to a fragrance accord that is free from extraneous matter. A neat fragrance accord comprises only perfume raw materials and is unencapsulated and/or unbound from other compounds that would cause a delay in the release of the perfume raw materials of the fragrance accord.

"Perfume raw material" refers to a single individual chemical compound that is odiferous.

The present disclosure includes absorbent articles comprising fragrance accords and functional lotion compositions. In particular, the present disclosure includes absorbent articles having different fragrance accords and different functional lotion compositions to meet the needs of various types of consumers.

A consumer may have multiple scent experiences during use of an absorbent article, such as a wipe. For example, one scent experience may occur as the consumer opens the package of wipes and removes a wipe from the package. Another scent experience may occur as the consumer cleans a baby's skin to remove soils. In addition, another scent experience may occur as a result of scent that lingers on the skin of the baby and/or the consumer after cleaning the baby's skin.

Different consumers may prefer different potencies of scent during each scent experience. For example, one type of consumer may prefer a noticeable amount of scent during each scent experience. More specifically, this same type of consumer may want enough scent present on the absorbent article such that the scent is noticeable as the absorbent article is removed from the package and such that the scent may be perceived over the smell of a soil during the cleaning process. Further, this same type of consumer may want a lingering scent left on the skin of the baby and/or the consumer after using the absorbent article.

Another type of consumer may want a less potent scent present on an absorbent article than the type of consumer previously described. For example, this type of consumer may want just enough scent to be detectable, without the scent being overwhelming, as the absorbent article is removed from the package. During the cleaning process, this type of consumer may want to experience a noticeable amount of scent that signals that the skin is clean and fresh, but again without the scent from the absorbent article overwhelming the experience. This consumer may want little to no lingering scent left on the baby's and/or the consumer's skin after use of the absorbent article.

Further to the above, the absorbent article, such as a wipe, may also provide consumers with multiple tactile interactions. For example, consumers first feel the absorbent article as it is removed from a package. Additionally, the consumers use the absorbent article to clean the skin by removing soils. Furthermore, consumers may perceive and/or feel a residue on the skin after cleaning.

Different consumers may prefer different functional lotion compositions. For example, one type of consumer may prefer a noticeable amount of lotion during each tactile interaction. More specifically, this type of consumer may want enough lotion present on the absorbent article such that the lotion is noticeable as the absorbent article is removed from the package and such that the lotion provides a lubricious and/or creamy-feel. This type of consumer may also want the lotion to have a lingering effect on the skin of the baby and/or the consumer after using the absorbent article. For example, the absorbent article may provide an actual and/or a perceivable residue on the skin, much like a moisturizing cream.

Another type of consumer may prefer a different functional lotion composition to be present on an absorbent article than the type of consumer previously described. This type of consumer may want a relatively low amount of lotion present on the absorbent article so that as the consumer removes the absorbent article from the package, the absorbent article feels lightweight and watery. For example, this type of consumer may want just enough lotion to be detectable. During the cleaning process, this type of consumer may want to experience a noticeable amount of lotion that signals that the skin is clean and fresh, but without the lotion from the absorbent article overwhelming the experience. Further, this type of consumer may want little to no lingering lotion left on the skin after use of the absorbent article.

Consumer research has suggested that consumers who prefer a more noticeable, lingering scent also prefer a more lubricious, creamy-feeling lotion. This type of consumer may be referred to herein as a heavy experience seeking consumer. Further, a consumer who prefers a lighter, less noticeable scent also prefers a lightweight, watery lotion. This type of consumer may be referred to herein as a light experience seeking consumer.

In order to meet the needs of these two distinct types of consumers, the present disclosure includes an array of absorbent articles, such as wipes, comprising a functional lotion composition including different fragrance accords paired with different lotion formulas. The array of absorbent articles may include a first absorbent article having a first fragrance accord and a first lotion formula, and a second absorbent article having a second fragrance accord and a second lotion formula. The first functional lotion composition may be different from the second functional lotion composition. More specifically, first fragrance accord may be different from the second fragrance accord, and/or the first lotion formula may be different from the second lotion formula. The array of absorbent articles may be commonly-branded and/or commonly-sourced.

The lotion compositions described herein are referred to as functional because the lotion provides a certain type of experience for the consumer. For example, a particular functional lotion composition may provide an experience of lubriciousness and/or cleanliness.

While the following disclosure discusses functional lotion compositions including fragrance accords and lotion formulas in combination with wipes, it is to be appreciated that the functional lotion compositions of the present disclosure may be used with various types of absorbent articles, including diapers, wipes, tissues, feminine hygiene products, adult incontinence products, and cleaning articles.

Fragrance Accord

Absorbent articles of the present disclosure may include a functional lotion composition including a fragrance accord. The fragrance accord may comprise a perfume raw material or a mixture of different perfume raw materials. Perfume raw materials may be characterized by vapor pressure (VP) or Kovats Index (KI). As used herein, "vapor pressure" refers to an estimated vapor pressure provided by EPI Suite, version 4.0, available from U.S. Environmental Protection Agency.

Perfume raw materials of the present disclosure may be classified as top notes, middle notes, or base notes based upon the relative volatility of a particular perfume raw material. Perfume raw materials having a vapor pressure of greater than 0.08 Torr at 25° C. or a Kovats Index of less than 1300 are classified as "top notes". Perfume raw materials having a vapor pressure between 0.006 Torr and 0.08 Torr at 25° C. or a Kovats Index between 1300 and 1450 are classified as "middle notes". Perfume raw materials having a vapor pressure less than or equal to 0.006 Torr at 25° C. or a Kovats Index of greater than 1450 are classified as "base notes". Top notes are the most volatile and, therefore, provide an initial "burst" of fragrance that dissipates relatively quickly. Middle notes are less volatile than top notes and may be detected for a longer period of time than top notes. Base notes are the least volatile and may be detected for the longest period of time.

In some exemplary configurations, in order to meet the needs of a light experience seeking consumer, an absorbent article may comprise a functional lotion composition including a perfume accord comprising a higher percentage of middle notes as compared with the percentages of top and base notes. For example, an absorbent article may include a fragrance accord comprising from about 10% to about 15%, by total weight, of a perfume raw material having a vapor pressure of greater than 0.08 Torr at 25° C.; from about 35% to about 65%, by total weight, of a perfume raw material having a vapor pressure from 0.006 Torr at 25° C. to 0.08 Torr at 25° C.; and from about 20% to about 30%, by total weight, of a perfume raw material having a vapor pressure of less than 0.006 Torr at 25° C. In another example, an absorbent article may include a fragrance accord comprising from about 10% to about 15%, by total weight, of a perfume raw material having a Kovats Index of less than 1300; from about 35% to about 65%, by total weight, of a perfume raw material having a Kovats Index from 1300 to 1450; and from about 20% to about 30%, by total weight, of a perfume raw material having a Kovats Index of greater than 1450. Without wishing to be bound by theory, it is believed that a perfume accord having a relatively greater proportion of middle notes than top or base notes may provide light experience seeking consumers with enough scent as the absorbent article is removed from the package and during use without being overwhelming while minimizing the amount of scent that will be left on the skin after use of the absorbent article.

In another exemplary configuration, in order to meet the needs of a heavy experience seeking consumer, an absorbent article may include a functional lotion composition including a perfume accord comprising the highest percentage of base notes and the lowest percentage of top notes. For example, an absorbent article may include a fragrance accord comprising from about 10% to about 20%, by total weight, of a perfume raw material having a vapor pressure of greater than 0.08 Torr at 25° C.; from about 20% to about 30%, by total weight, of a perfume raw material having a vapor pressure from about 0.006 Torr at 25° C. to 0.08 Torr at 25° C.; and from about 45% to about 70%, by total weight, of a perfume raw material having a vapor pressure of less than 0.006 Torr at 25° C. In another example, an absorbent article may comprise from about 10% to about 20%, by total weight, of a perfume raw material having a Kovats Index of less than 1300; from about 20% to about 30%, by total weight, of a perfume raw material having a Kovats Index from 1300 to 1450; and from about 45% to about 70%, by total weight, of a perfume raw material having a Kovats Index of greater than 1450. Without wishing to be bound by theory, it is believed that a fragrance accord having the lowest percent of top notes, a higher percentage of middle notes, and the highest percentage of base notes may provide heavy experience seeking consumers with a relatively high amount of scent as the absorbent article is removed from the package, a scent that may be perceived over the scent of the soil being removed, and a lingering scent that remains on the skin after using the absorbent article.

The present disclosure may include an array of absorbent articles to meet the needs of heavy experience seeking consumers and light experience seeking consumers. In some embodiments, the array of absorbent articles may include a first absorbent article having a first functional lotion composition comprising a first fragrance accord. The first fragrance accord may comprise from about 10% to about 15%, by total weight, of a perfume raw material having a vapor pressure of greater than 0.08 Torr at 25° C.; from about 35% to about 65%, by total weight, of a perfume raw material having a vapor pressure from 0.006 Torr at 25° C. to 0.08 Torr at 25° C.; and from about 20% to about 30%, by total weight, of a perfume raw material having a vapor pressure of less than 0.006 Torr at 25° C. The array may comprise a second absorbent article having a second functional lotion composition comprising a second fragrance accord. The second fragrance accord may comprise from about 10% to about 20%, by total weight, of a perfume raw material having a vapor pressure of greater than 0.08 Torr at 25° C.; from about 20% to about 30%, by total weight, of a perfume raw material having a vapor pressure from 0.006 Torr at 25° C. to 0.08 Torr at 25° C.; and from about 45% to about 70%, by total weight, of a perfume raw material having a vapor pressure of less than 0.006 Torr at 25° C.

In some exemplary embodiments, an array of absorbent articles may include a first absorbent article having a first functional lotion composition including a first fragrance accord. The first fragrance accord may comprise from about 10% to about 15%, by total weight, of a perfume raw material having a Kovats Index of less than 1300; from about 35% to about 65%, by total weight, of a perfume raw material having a Kovats Index from 1300 to 1450; and from about 20% to about 30%, by total weight, of a perfume raw material having a Kovats Index of greater than 1450. The array may include a second absorbent article having a second functional lotion composition including a second fragrance accord. The second fragrance accord may comprise from about 10% to about 20%, by total weight, of a perfume raw material having a Kovats Index of less than 1300; from about 20% to about 30%, by total weight, of a perfume raw material having a Kovats Index from 1300 to 1450; and from about 45% to about 70%, by total weight, of a perfume raw material having a Kovats Index of greater than 1450.

Exemplary top note perfume raw materials of the present disclosure include Prenyl acetate, Dihydro Myrcenol, Ethyl acetate, cis-3-Hexenal, beta Pinene, Eucalyptol, Benzaldehyde, Phenyl acetaldehyde, Melonal, Orange Terpenes, and Amyl Propionate. It is to be appreciated that various other top note perfume raw materials may be used in the fragrance accord of the present disclosure.

Exemplary middle note perfume raw materials of the present disclosure include Mayol, 4-tertiary Butyl Cyclohexyl Acetate, Patchone, Coumarin, Phenyl Ethyl Acetate, Terpinyl acetate, Cinnamic Alcohol, Nonalactone, Dimethyl Benzyl Carbinyl Acetate, Heliotropin, and Undecavertol. It is to be appreciated that various other middle note perfume raw materials may be used in the fragrance accord of the present disclosure.

Exemplary base note perfume raw materials of the present disclosure include Methyl Cedrylone, Eugenol, Frutene, Helional, Sandalore, Helvetolide, Iso E Super, Ethyl Vanillin, Karanal, Amyl Salicylate, and Benzoin. It is to be appreciated that various other base note perfume raw materials may be used in the fragrance accord of the present disclosure.

The fragrance accords of the present disclosure may be "neat".

The fragrance accords of the present disclosure may include various perfume raw materials having various characters, including light, fresh, fruity, citrus, green, floral, watery, powdery, gourmand, woody, oriental, herbal, marine, ozonic, amber, musk, aldehydic, aromatic, spice, balsamic, sweet, and the like.

Lotion Formula

Absorbent articles of the present disclosure may include a functional lotion composition. The functional lotion composition may include various fragrance accords of the present disclosure and a lotion formula. The functional lotion composition may be characterized by peak viscosity and average peak dynamic frictional force. More specifically, the functional lotion composition may have a peak viscosity as measured according to the Peak Complex Viscosity Test Method and an average peak dynamic frictional force as measured according to the Multi-Cycle Dynamic Friction Force Method. Generally, the lotion formula of the functional lotion composition is what most greatly affects the peak viscosity and the average peak dynamic frictional force.

A functional lotion composition having a relatively high peak viscosity and a relatively low average peak dynamic frictional force may be perceived as being lubricous and/or creamy-feeling. A functional lotion composition having a relatively low peak viscosity and a relatively high average peak dynamic frictional force may be perceived as being watery and/or lightweight.

In some exemplary configurations, in order to meet the needs of heavy experience seeking consumers, who want an absorbent article having a creamy, lubricious feel, an absorbent article may comprise a functional lotion composition having a relatively higher peak viscosity and a relatively lower average peak dynamic frictional force. For example, an absorbent article may include a lotion composition comprising a peak viscosity greater than about 65 mPa·s and/or from about 75 mPa·s to about 200,000 mPa·s and/or from about 80 mPa·s to about 100,500 mPa·s and/or from about 100 mPa·s to about 100,250 mPa·s, including all 0.1 increments therebetween. The absorbent article may also impart an average peak dynamic frictional force from about 2.5 g to about 27.5 g and/or about 5 g to about 25 g and/or about 10 g to about 22.5 g, including all 0.1 increments therebetween. Without wishing to be bound by theory, it is believed that a lotion composition having a peak viscosity greater than about 75 mPa·s and an average peak dynamic frictional force less than about 27.5 g may provide heavy experience seeking consumers with enough tactile interaction during use of the absorbent article to be identifiable by the consumer, and while providing a residue that may be left on the skin or may be perceived to be left on the skin after use of the absorbent article.

In another exemplary configuration, in order to meet the needs of light experience seeking consumers, who want an absorbent article having a watery and lightweight feel, an absorbent article may comprise a lotion composition having a relatively lower peak viscosity and a relatively higher average peak dynamic frictional force. For example, an absorbent article may include a lotion composition having a peak viscosity from 5 mPa·s to about 65 mPa·s and/or from about 5 mPa·s to about 60 mPa·s and/or from about 15 mPa·s to about 55 mPa·s and/or from about 20 mPa·s to about 50 mPa·s, including all 0.1 increments therebetween, and an average peak dynamic frictional force from about 22 g to about 60 g and/or from about 25.5 g to about 55 g and/or from about 27.5 g to about 52.5 g, including all 0.1 increments therebetween. Without wishing to be bound by theory, it is believed that a lotion composition having a peak viscosity less than about 65 mPa·s and an average peak dynamic frictional force greater than about 25 g may provide light experience seeking consumers with enough tactile interaction during use of the absorbent article to be noticeable by the consumer, and while leaving relatively small amounts of residue to no perceived residue on the skin after use of the absorbent article.

Figure 5:
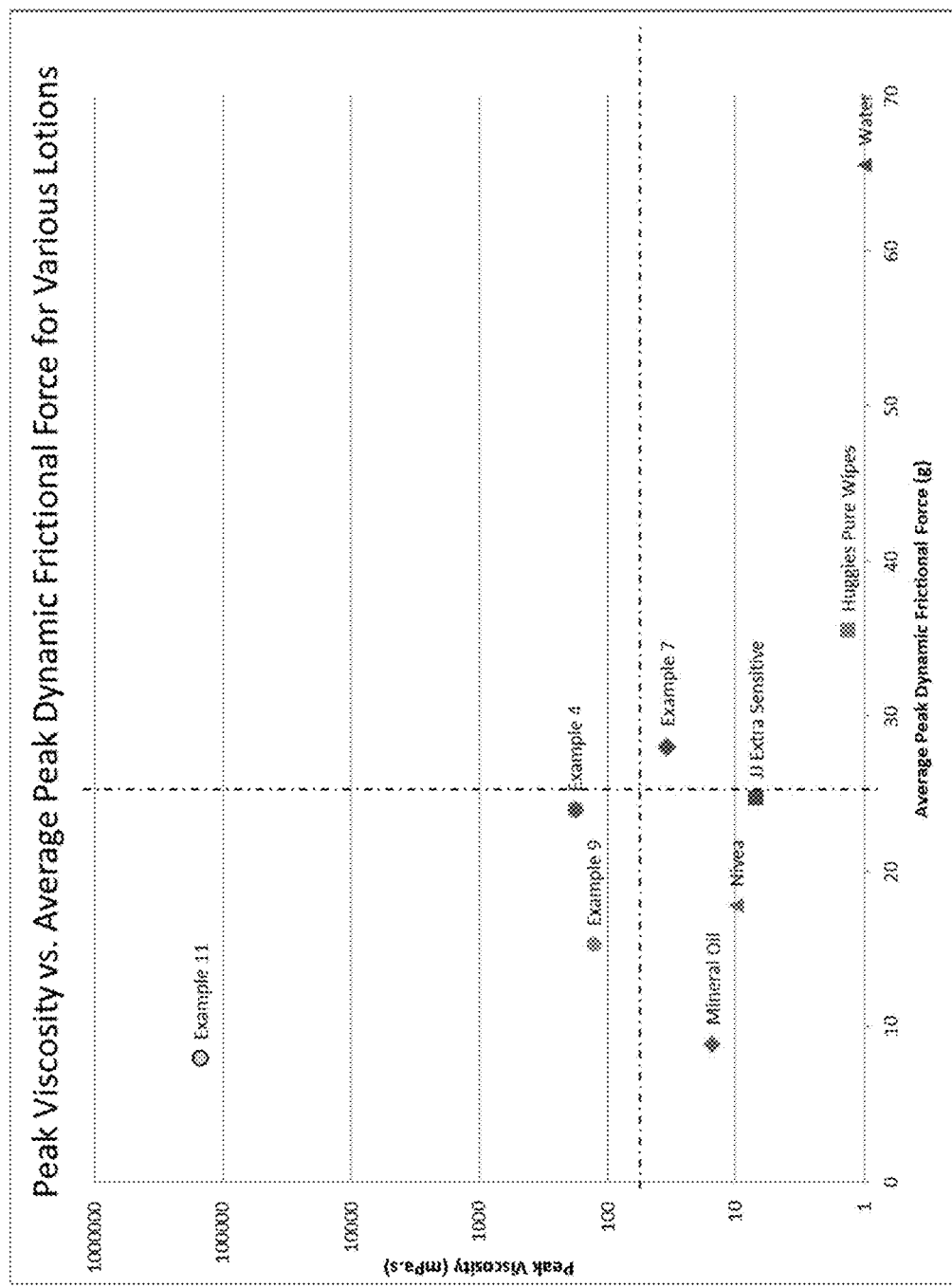
FIG. 5 is a plot of peak viscosity vs. average peak dynamic frictional force for various lotion formulas.

FIG. 5 illustrates examples of various lotion compositions having a peak viscosity of greater than 65 mPa·s and an average peak dynamic frictional force of less than 25 g, which may appeal to heavy experience seeking consumers, and a peak viscosity of less than 60 mPa·s and an average peak dynamic frictional force of greater than 25 g, which may appeal to light experience seeking consumers. The data points labeled as Example 4, Example 9, and Example 7 are described below.

In order to provide an absorbent article, such as a wipe, that meets the needs of both a heavy experience seeking consumer and a light experience seeking consumer, an array of absorbent articles may be offered for sale. The array of absorbent articles may include a first absorbent article having a first functional lotion composition, which appeals to light experience seeking consumers. The first functional lotion composition may have a peak viscosity from about 5 mPa·s to about 65 mPa·s and an average peak dynamic frictional force from about 25 g to about 60 g. The array may comprise a second absorbent article having a second functional lotion composition, which appeals to heavy experience seeking consumers. The second functional lotion composition may have a peak viscosity greater than about 75 mPa·s and an average peak dynamic frictional force from about 2.5 g to about 25 g. Generally, the first functional lotion composition may have a peak viscosity that is less than the peak viscosity of the second functional lotion composition. The first function lotion composition may also have an average peak dynamic frictional force that is greater than the average peak dynamic frictional force of the second functional lotion composition.

As previously stated, the functional lotion composition may include various fragrance accords of the present disclosure and a lotion formula. More specifically, the first functional lotion composition may include a first fragrance accord and a first lotion formula and the second functional lotion composition may include a second fragrance accord and a second lotion formula. The first lotion composition may differ from the second lotion composition in that the first lotion formula is different from the second lotion formula.

Exemplary functional lotion compositions having a peak viscosity of less than about 65 mPa·s and an average peak dynamic frictional force greater than 25 g of the present disclosure include, for example, lotion formulas as included in Examples 4, 5, and 6, below. It is to be appreciated that various other functional lotion compositions may be used to obtain the peak viscosity of the present disclosure.

Exemplary functional lotion compositions having a peak viscosity of greater than about 75 mPa·s and an average peak dynamic frictional force less than 27.5 g of the present disclosure include, for example, lotion formulas as included in Examples 7 through 11, below. It is to be appreciated that various other functional lotion compositions may be used to obtain the peak viscosity of the present disclosure.

The functional lotion composition may be aqueous or emulsion-based. The pH of the composition may be from about pH 3, 4, or 5 to about pH 7, 7.5, or 8. In some exemplary configurations, the pH may be from about 3.5 to about 4.1.

Glucomannan

In some exemplary configurations, the lotion formula may comprise a glucomannan. Without being bound by theory, it is believed that a cleansing composition comprising a glucomannan improves the cleaning performance of a wet wipe. Without wishing to be bound by theory, using a cleansing composition comprising a glucomannan in a wet wipe may increase the adhesive interaction between the soil and the wet wipe above the adhesive interaction between the soil and the surface, thereby allowing the soil to detach from the surface upon wiping. The lotion formula may comprise from about 0.01%, by total weight, to about 0.50%, by total weight, of a glucomannan. The lotion formula may include a glucomannan and one or more synergy enhancing agents. Non-limiting examples of synergy enhancing agents include xanthan gum, carrageenan, alginate, locust bean gum, starch, and gellan gum.

The lotion formula may comprise from about 0.1%, by total weight, to about 0.5%, by total weight, or from about 0.12%, by total weight, to about 0.18%, by total weight, of one or more synergy enhancing agents. The ratio of glucomannan to synergy enhancing agent present in the lotion formula may be from about 1:1.5 to about 1:10. Exemplary compositions comprising glucomannan and a synergy enhancing agent are described in U.S. Provisional Patent Application No. 61/758,802.

An exemplary wet wipe may include a lotion formula comprising glucomannan and xanthan gum. Another exemplary wet wipe may include a lotion formula comprising glucomannan, carrageenan, and xanthan gum. In a lotion formula comprising glucomannan, carrageenan, and xanthan gum, the ratio of xanthan gum to glucomannan to carrageenan may be from about 1:0.02:0.03 to about 1:0.33:0.5.

The peak complex viscosity of a lotion formula comprising a glucomannan and a synergy enhancing agent for use in a wet wipe may be greater than about 0.8 Pascal·seconds (hereinafter "Pa·s"), greater than 2.5 Pa·s, or greater than about 3.0 Pa·s. The peak complex viscosity of a lotion formula for use in a wet wipe may be in the range of about 1.0 Pa·s to about 5.0 Pa·s.

In addition, the lotion formula may include various optional ingredients, such as surfactants, emollients, filmformers, preservatives, pH buffers, rheology modifiers, and various other adjunct ingredients, such as described in U.S. Pat. Nos. 7,666,827; 7,005,557; 8,221,774; and U.S. Patent Application Publication No. 2011/0268777. It is to be noted that some ingredient compounds can have a multiple function and that all compounds are not necessarily present in the lotion formula.

Emollient

The lotion formula may include an emollient. Emollients may (1) hydrate the residues (for example, fecal residues or dried urine residues or menses), thus enhancing their removal from the skin, (2) hydrate the skin, thus reducing its dryness and irritation while improving its flexibility under the wiping movement, (3) reduce the adhesive interaction between the soil and the surface, and (4) protect the skin from later irritation (for example, caused by the friction of an absorbent article) as the emollient is deposited onto the skin and remains at its surface as a protective layer.

An emollient may include silicone oils, functionalized silicone oils, hydrocarbon oils, fatty alcohols, fatty alcohol ethers, fatty acids, esters of monobasic and/or dibasic and/or tribasic and/or polybasic carboxylic acids with mono and polyhydric alcohols, polyoxyethylenes, polyoxypropylenes, mixtures of polyoxyethylene and polyoxypropylene ethers of fatty alcohols, and mixtures thereof. The emollients may be either saturated or unsaturated, have an aliphatic character and be straight or branched chained or contain alicyclic or aromatic rings.

In some exemplary configurations, the lotion formula may comprise a mixture of caprylic/capric triglycerides in combination with Bis-PEG/PPG-16/16 PEG/PPG-16/16 dimethicone known as ABIL® CARE 85, available from Degussa Care Specialties of Hopewell, Va.

Various oil materials may function as emollients, while also providing skin benefits, including improving or maintain the integrity of the skin. For example, the lotion formula may comprise an omega-6 fatty acid. The lotion formula may comprise at least about 0.003%, from about 0.003% to about 35%, from about 0.015% to about 25%, or from about 0.06% to about 20%, by total weight, of the lotion and/or coating composition, of omega-6 fatty acid. Exemplary lotion compositions comprising omega-6 fatty acids are described in U.S. Patent Publication No. 2011/0159074 A1.

The omega-6 fatty acid may be added to the lotion formula as an oil material, such as from a vegetable oil. Therefore, in one exemplary configuration, the lotion formula comprises an oil material comprising omega-6 fatty acid. The lotion formula may comprise from about 0.1% to about 70%, from about 0.5% to about 50%, or from about 2% to about 40%, by total weight, of the lotion and/or coating composition, of the oil material. The oil material may comprise at least 3%, from about 3% to about 50%, or from about 5% to about 40%, by total weight, of the oil material, of omega-6 fatty acid.

Non-limiting examples of suitable oil materials include high oleic canola Oil (*Brassica campestris, B. napus, B. rapa*; characterized by having an oleic fatty acid content greater than 70%, e.g., high oleic canola oil, very high oleic canola oil, or partially hydrogenated canola oil), marula kernel oil (*Sclerocarya birrea*), palm oil (*Elaeis Guineensis* Oil), palm olein, palm stearin, palm superolein, pecan oil, pumpkin seed oil, oleic safflower oil (*Carthamus Tinctorius*; characterized by having an oleic fatty acid content of greater than about 30% and omega-6 fatty acid content of less than about 50%, e.g., high oleic safflower oil), sesame oil (*Sesamum indicum, S. oreintale*), soybean oil (*Glycine max*, e.g., high oleic soybean, low linolenic soybean oil, partially hydrogenated), high oleic sunflower oil (*Helianthus annus*; characterized by having an oleic content of greater than about 40%, e.g., mid oleic sunflower or high oleic sunflower oil), and mixtures thereof. Oleic canola oil, palm oil, sesame oil, high oleic safflower oil, high oleic soybean oil, mid oleic sunflower oil, and high oleic sunflower oil are common plant-bred derived oils and may be also be derived from non-genetically modified organisms (non-GMO).

Non-limiting examples of oil materials are commercially-available from a number of vendors, including Cargill for partially hydrogenated soybean oil (i.e., PREFERENCE 110W Soybean Oil or Preference® 300 Hi Stability Soybean Oil), mid oleic sunflower oil (i.e., NUSUN Mid-Oleic Sunflower Oil), high oleic sunflower oil (i.e., CLEAR VALLEY High Oleic Sunflower Oil), high oleic canola oil, very high oleic canola, and partially hydrogenated low erucic rapeseed oil (i.e., CLEAR VALLEY 65 High Oleic Canola Oil and CLEAR VALLEY 75 High Oleic Canola Oil); Lambert Technology for high oleic canola oil (i.e., Oleocal C104); Arch Personal Care for manila kernel oil; Pioneer for high oleic soybean oil (i.e., PLENISH®); Asoyia for low linolenic soybean oil (i.e., ULTRA LOW LINOLENIC SOYBEAN OIL); and Dipasa, Inc. for refined sesame oil.

The oil material can further comprise a blend of oils, including those described supra, as well as additional oil materials. Suitable additional oil materials can include acai berry oil, almond oil, avocado oil, beech oil, brazil nut oil, camelina sativa oil (family Brassicaceae, e.g., Camelina Sativa, Gold of Pleasure, False Flax, etc.), camellia seed oil, canola oil, carrot seed oil, cashew nut oil, caster oil, cherry kernel oil, chia oil, corn oil, cottonseed oil, hydrogenated cottonseed oil, evening primrose oil, filbert (hazelnut) oil, grapeseed oil, hemp oil, hickory nut oil, jojoba oil, kukui oil, lanolin, olive oil (Olea europaea), macadamia oil, maringa oil, meadowfoam oil, neem oil, palm kernel oil, olive oil, passionflower oil (family Passiflora, Passiflora Incarnata), peanut oil, peach kernel oil, pistachio nut oil, rapeseed oil, rice bran oil, rose hip oil, safflower oil, sorghum oil, soybean oil, sunflower seed oil, tall oil, vegetable oil, vegetable squalene, walnut oil, wheat germ oil, and mixtures thereof. The oil material of the present invention can be selected from the group consisting of camelina sativa seed oil, oleic canola oil, evening primrose oil, marula kernel oil, palm oil, palm olein, palm stearin, palm superolein, passiflora incarnata seed oil, pecan oil, pumpkin seed oil, oleic safflower oil, sesame oil, soybean oil, oleic sunflower oil, vegetable oil, and mixtures thereof.

Suitable, commercially available oil materials include a mixture of vegetable oil and camelina sativa seed oil (commercially-available as LIPEX Omega 3/6 from Aarhus Karlshamn Sweden AB), a mixture of vegetable oil and passiflora incarnata seed oil (commercially-available as LIPEX Omega Passiflora from Aarhus Karlshamn Sweden AB), a mixture of vegetable oil and evening primrose oil (commercially-available as LIPEX Omega EPO from Aarhus Karlshamn Sweden AB), high oleic canola oil (commercially-available as CLEAR VALLEY 75 High Oleic Canola Oil from Cargill), and mixtures thereof.

Surfactant

The lotion formula may include one or more surfactants. The surfactant can be an individual surfactant or a mixture of surfactants. The surfactant may be a polymeric surfactant or a non-polymeric one. The surfactant may aid in dissolution and removal of the soils from the surface being cleansed. The surfactant or combinations of surfactants may be mild, which means that the surfactants provide sufficient cleaning or detersive benefits but do not overly dry or otherwise harm or damage the skin. The surfactant, when present in the functional lotion composition, may be present in an amount ranging from about 0.5%, 1%, or 4%, by total weight, to about 0.001%, 0.01% or 0.02%, by total weight, of the functional lotion composition. The surfactant may comprise PEG-40 Hydrogenated Castor Oil, manufactured by Clariant International Ltd. of Switzerland under the designation EMULSOGEN HCW049.

A wide variety of surfactants are useful herein and include those selected from the group consisting of anionic surfactants, nonionic surfactants, cationic surfactants, amphoteric surfactants, zwitterionic surfactants, and mixtures thereof.

A wide variety of anionic surfactants are useful herein. Non-limiting examples of anionic surfactants include those selected from the group consisting of carboxylates, sarcosinates, sulfates, sulfonates, isethionates, taurates, phosphates, lactylates, glutamates, and mixtures thereof.

Nonionic surfactants useful herein include, but are not limited to, those selected from the group consisting of alkyl glucosides, alkyl polyglucosides, polyhydroxy fatty acid amides, alkoxylated fatty acid esters, alkoxylated fatty alcohol ethers, sucrose esters, and mixtures thereof.

Amphoteric surfactants suitable for use in the present compositions include those surfactants broadly described as derivatives of aliphatic secondary and tertiary amines in which the aliphatic radical can be straight or branched chain and wherein one of the aliphatic substituents contains from about 8 to about 18 carbon atoms and one contains an anionic water solubilizing group such as carboxy, sulfonate, sulfate, phosphate, or phosphonate. Useful amphoteric surfactants include the group consisting of cocoamphoacetate, cocoamphodiacetate, lauroamphoacetate, lauroamphodiacetate, and mixtures thereof.

Zwitterionic surfactants suitable for use herein include those surfactants broadly described as derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one contains an anionic group such as carboxy, sulfonate, sulfate, phosphate or phosphonate. Useful zwitterionic surfactants include betaines, amphoacetates and sulfobetaines, e.g., cocoamidopropylbetaine, sodium laurylamphoacetate and cocoamidopropylhydroxysultaine.

Rheology Modifier

The lotion formula may comprise one or more rheology modifiers. A rheology modifier may (1) help to stabilize the lotion composition on a substrate, (2) enhance the transfer of the lotion composition to the skin, and (3) enhance the uniformity of the layer of the lotion composition on the skin. For example, rheology modifiers may help to preserve a homogeneous distribution of the lotion composition within a stack of the substrates. Any composition that is in fluid form may have a tendency to migrate to the lower part of the wipes stack during prolonged storage. This effect may create an upper part of the stack of substrates having less lotion composition than the bottom part of the stack.

Non-limiting examples of rheology modifiers include, but are not limited to, rheology modifiers comprising: polysaccharide units, e.g., cellulose, xanthan gum, diutan gum, carrageenan, gellan gum, welan gum, pectin, sclerotium gum, starch, galactoarabinan, alginate, and modified-forms thereof homopolymers of acrylic acid; acrylic acid crosslinked with a polyfunctional compound, e.g., carbomer and acrylate crosspolymer; copolymers of acrylic acid, acrylate esters, maleic acid and the like, generally known as the alkali swellable emulsions (ASE) group; hydrophobically-modified copolymers of acrylic acid, acrylate esters, maleic acid and the like, generally known as the hydrophobically-modified alkali swellable emulsions (HASE) group; polyethylene glycol units of varying length connected by urethane linkages and terminated with hydrophobic end groups, generally known as the hydrophobically-modified ethoxylated urethane resins (HEUR) group; organoclays; silicas; and combinations thereof.

Rheology modifiers, when present in the functional lotion composition, may be present in the range of about 0.01%, 0.015%, or 0.02%, by total weight, to about 2%, by total weight, of the functional lotion composition.

Preservative

Controlling microbiological growth may be beneficial in water based products such as functional lotion compositions intended for use in wet wipes. The functional lotion composition may comprise a preservative or a combination of preservatives acting together as a preservative system. Preservatives and preservative systems are used interchangeably in the present disclosure to indicate one unique or a combination of preservative compounds. A preservative may be understood to be a chemical or natural compound or a combination of compounds reducing the growth of microorganisms, thus enabling a longer shelf life for a package of substrates (opened or not opened) as well as creating an environment with reduced growth of microorganisms when transferred to the skin during the wiping process.

The spectrum of activity of the preservative may include bacteria, molds and yeast. Each of such microorganisms may be killed by the preservative. Another mode of action to be contemplated may be the reduction of the growth rate of the microorganisms without active killing. Both actions however result in a drastic reduction of the population of microorganisms.

Materials useful as preservatives include sorbitan caprylate, methylol compounds, iodopropynyl compounds, simple aromatic alcohols, paraben compounds, benzyl alcohol, benzoic acid, benzoates, sorbic acid, sorbates, phenoxyethanol, ethxylhexyglycerin, chelators such as ethylenediamine tetraacetic acid, and combinations thereof. Suitable preservative systems are described in U.S. Patent Publication Nos. 2015/0017218; 2005/0008680; and 2005/0008681; and U.S. Application No. 62/057,297 filed Sep. 30, 2014.

Low pH buffering systems, such as a citrate-citric acid buffering system at a pH of less than about 5, may also be employed as part of the preservative system.

In some exemplary configurations, the preservative system may comprise simple aromatic alcohols (e.g., benzyl alcohol). Materials of this type may have effective antibacterial activity. Benzyl alcohol is available from Symrise, Inc. of Teterboro, N.J. In other exemplary configurations, the preservative system may comprise a mixture of benzyl alcohol, sodium benzoate, phenoxyethanol, ethylhexylglycerin, ethylenediamine tetraacetic acid, citric acid, and sodium citrate dehydrate wherein the pH of the lotion composition is less than about 4. The total concentration of benzyl alcohol may be lower than about 0.4%, by total weight, of the functional lotion composition. The total concentration of sodium benzoate may be lower than about 0.3%, by total weight, of the functional lotion composition. The combination of phenoxyethanol and ethylhexylglycerin, which are available as EUXYL® PE 9010 from Schulke & Mayr GmbH of Germany, may be lower than about 0.4%.

In some exemplary configurations, acidic compounds used in sufficient amount to reduce the pH of the functional lotion composition (e.g., pH of less than about 5) may be useful as the preservative, or as a potentiator for other preservative ingredients.

In other exemplary configurations, chelators, such as ethylenediamine tetraacetic acid and its salts, may also be used in preservative systems as a potentiator for other preservative ingredients.

Adjunct Ingredients

The lotion formula may optionally include other adjunct ingredients. Possible adjunct ingredients may be selected from a wide range of additional ingredients such as texturizers, colorants, soothing agents and medically active ingredients, such as healing actives and skin protectants.

Wipe

Various fragrance accords and lotion formulas of the present disclosure may be incorporated into an absorbent article such as a wipe. "Wipe" may be a general term to describe a piece of material, generally a non-woven material, used in cleansing hard surfaces, food, inanimate objects, toys, and body parts. In particular, many currently available wipes may be intended for the cleansing of the perianal area after defecation. Other wipes may be available for the cleansing of the face or other body parts. Multiple wipes may be attached together by any suitable method to form a mitt.

The wipe may comprise a substrate. The material from which a wipe is made should be strong enough to resist tearing during normal use, yet still provide softness to the user's skin, such as a child's tender skin. Additionally, the material should be at least capable of retaining its form for the duration of the user's cleansing experience.

Wipes may be generally of sufficient dimension to allow for convenient handling. Typically, the wipe may be cut and/or folded to such dimensions as part of the manufacturing process. In some instances, the wipe may be cut into individual portions so as to provide separate wipes which are often stacked and interleaved in consumer packaging. In other exemplary configurations, the wipes may be in a web form where the web has been slit and folded to a predetermined width and provided with means (e.g., perforations) to allow individual wipes to be separated from the web by a user. Suitably, an individual wipe may have a length between about 100 mm and about 250 mm and a width between about 140 mm and about 250 mm. In one exemplary configuration, the wipe may be about 200 mm long and about 180 mm wide and/or about 180 mm long and about 180 mm wide and/or about 170 mm long and about 180 mm wide and/or about 160 mm long and about 175 mm wide. The material of the wipe may generally be soft and flexible, potentially having a structured surface to enhance its cleaning performance.

It is also within the scope of the present disclosure that the wipe may be a laminate of two or more materials. Commercially available laminates, or purposely built laminates would be within the scope of the present disclosure. The laminated materials may be joined or bonded together in any suitable fashion, such as, but not limited to, ultrasonic bonding, adhesive, glue, fusion bonding, heat bonding, thermal bonding and combinations thereof. In another alternative exemplary configuration of the present disclosure the wipe may be a laminate comprising one or more layers of nonwoven materials and one or more layers of film. Examples of such optional films, include, but are not limited to, polyolefin films, such as, polyethylene film. An illustrative, but non-limiting example of a nonwoven material is a laminate of a 16 gsm nonwoven polypropylene and a 0.8 mm 20 gsm polyethylene film.

The wipes may also be treated to improve the softness and texture thereof by processes such as hydroentanglement or spunlacing. The wipes may be subjected to various treatments, such as, but not limited to, physical treatment, such as ring rolling, as described in U.S. Pat. No. 5,143,679; structural elongation, as described in U.S. Pat. No. 5,518,801; consolidation, as described in U.S. Pat. Nos. 5,914,084, 6,114,263, 6,129,801 and 6,383,431; stretch aperturing, as described in U.S. Pat. Nos. 5,628,097, 5,658,639 and 5,916,661; differential elongation, as described in WO Publication No. 2003/0028165 A1; and other solid state formation technologies as described in U.S. Publication No. 2004/0131820 A1 and U.S. Publication No. 2004/0265534 A1, and zone activation and the like; chemical treatment, such as, but not limited to, rendering part or all of the fibrous structure hydrophobic, and/or hydrophilic, and the like; thermal treatment, such as, but not limited to, softening of fibers by heating, thermal bonding and the like; and combinations thereof.

The wipe may have a basis weight of at least about 30 grams/m$^2$ and/or at least about 35 grams/m$^2$ and/or at least about 40 grams/m$^2$. In one example, the wipe may have a basis weight of at least about 45 grams/m$^2$. In another example, the wipe basis weight may be less than about 100 grams/m$^2$. In another example, wipes may have a basis weight between about 45 grams/m$^2$ and about 75 grams/m$^2$, and in yet another exemplary configuration a basis weight between about 45 grams/m$^2$ and about 65 grams/m$^2$.

The fibrous structures or wipes of the present disclosure may be saturation loaded with a liquid composition to form a wet wipe. The loading may occur individually, or after the wipes are placed in a stack, such as within a liquid impervious container or packet. In one example, the wet wipes may be saturation loaded with from about 1.5 g to about 6.0 g and/or from about 2.5 g to about 4.0 g of liquid composition per g of wipe. The liquid composition may exhibit a surface tension of from about 20 to about 35 and/or from about 28 to about 32 dynes/cm.

A plurality of the wet wipes may be stacked one on top of the other and may be contained in a container, such as a plastic tub or a film wrapper. The wipes may be folded and stacked. The wipes of the present disclosure may be folded in any of various known folding patterns, such as C-folding, Z-folding and quarter-folding. Use of a Z-fold pattern may enable a folded stack of wipes to be interleaved with overlapping portions. In one example, the stack of wet wipes (typically about 40 to 80 wipes/stack) may exhibit a height of from about 50 to about 300 mm and/or from about 75 to about 125 mm. The wet wipes may be stored long term in a stack in a liquid impervious container or film pouch without all of the lotion draining from the top of the stack to the bottom of the stack. The stack of wet wipes exhibits a saturation gradient index of from about 1.0 to about 2.0 and/or from about 1.0 to about 1.7 and/or from about 1.0 to about 1.5.

Alternatively, the wipes may include a continuous strip of material which has perforations between each wipe and which may be arranged in a stack or wound into a roll for dispensing, one after the other, from a container, which may be liquid impervious.

Substrate

"Substrate" refers herein to a material which is primarily two-dimensional (i.e., in an XY plane) and whose thickness (in a Z direction) is relatively small (i.e., 1/10 or less) in comparison to the substrate's length (in an X direction) and width (in a Y direction). Non-limiting examples of substrates include a web, layer or layers or fibrous materials, nonwovens, films and foils such as polymeric films or metallic foils. These materials may be used alone or may comprise two or more layers joined together. As such, a web is a substrate. The substrate may take the form of a wipe.

"Nonwoven" refers herein to a fibrous structure made from an assembly of continuous fibers, coextruded fibers, non-continuous fibers and combinations thereof, without weaving or knitting, by processes such as spunbonding, carding, meltblowing, airlaying, wetlaying, coforming, or other such processes known in the art for such purposes. As defined by EDANA, "nonwoven" means a sheet of fibers, continuous filaments, or chopped yarns of any nature or origin that have been formed into a web by any means, and bonded together by any means, with the exception of weaving or knitting. Felts obtained by wet milling are not nonwovens. Wetlaid webs are nonwovens provided that they contain a minimum of 50% by weight of man-made fibers, filaments or other fibers of non-vegetable origin with a length to diameter ratio that equals or exceeds 300 or a minimum of 30% by weight of man-made fibers, filaments or other fibers of non-vegetable origin with a length to diameter ratio that equals or exceeds 600 and a maximum apparent density of 0.40 g/cm$^3$.

"Fiber" and/or "Filament" as used herein means an elongate particulate having an apparent length greatly exceeding its apparent width, i.e., a length to diameter ratio of at least about 10. For purposes of the present invention, a "fiber" is an elongate particulate as described above that exhibits a length of less than 5.08 cm (2 in.) and a "filament" is an elongate particulate as described above that exhibits a length of greater than or equal to 5.08 cm (2 in.).

Non-limiting examples of processes for making a substrate include known wet-laid papermaking processes, air-laid papermaking processes including carded and/or spun-laced processes. Such processes typically include steps of preparing a fiber composition in the form of a suspension in a medium, either wet, more specifically aqueous medium, or dry, more specifically gaseous, i.e., with air as medium. The aqueous medium used for wet-laid processes is oftentimes referred to as a fiber slurry. The fibrous slurry is then used to deposit a plurality of fibers onto a forming wire or belt such that an embryonic fibrous structure is formed, after which drying and/or bonding the fibers together results in a fibrous structure. Further processing the fibrous structure may be carried out such that a substrate is formed.

The substrate may be a nonwoven material. The substrate may be homogeneous or may be layered. If layered, the substrate may comprise at least two and/or at least three and/or at least four and/or at least five layers. The nonwoven material may comprise one or more layers of such fibrous assemblies, wherein each layer may include continuous fibers, coextruded fibers, non-continuous fibers and combinations thereof.

The substrate of the present invention may include co-formed structure. "Co-formed structure" as used herein means that the structure comprises a mixture of at least two different materials wherein at least one of the materials comprises a filament, such as a polypropylene filament, and at least one other material, different from the first material, comprises a solid additive, such as a fiber and/or a particulate. In one example, a co-formed fibrous structure comprises solid additives, such as fibers, such as wood pulp fibers and/or absorbent gel materials and/or filler particles and/or particulate spot bonding powders and/or clays, and filaments, such as polypropylene filaments. "Solid additive" as used herein means a fiber and/or a particulate. "Particulate" as used herein means a granular substance or powder.

The substrate may include fibers comprised of any natural, cellulosic, and/or wholly synthetic material. Fibers are typically considered discontinuous in nature. Examples of natural fibers may include cellulosic natural fibers, such as fibers from hardwood sources, softwood sources, or other non-wood plants. The natural fibers may comprise cellulose, starch and combinations thereof. Non-limiting examples of suitable cellulosic natural fibers include wood pulp, northern softwood Kraft, southern softwood Kraft, CTMP, deinked, corn pulp, acacia, eucalyptus, aspen, reed pulp, birch, maple, radiata pine and combinations thereof. Other sources of natural fibers from plants include albardine, esparto, wheat, rice, corn, sugar cane, papyrus, jute, reed, sabia, raphia, bamboo, sidal, kenaf, abaca, sunn, rayon (also known as viscose), lyocell, cotton, hemp, flax, ramie, bagasse and combinations thereof. Yet other natural fibers may include fibers from other natural non-plant sources, such as, down, feathers, silk, cotton and combinations thereof. The natural fibers may be treated or otherwise modified mechanically or chemically to provide desired characteristics or may be in a form that is generally similar to the form in which they can be found in nature. Mechanical and/or chemical manipulation of natural fibers does not exclude them from what are considered natural fibers with respect to the development described herein.

The substrate may include synthetic fibers. The synthetic fibers can be any material, such as those selected from the group consisting of polyesters (e.g., polyethylene terephthalate), polyolefins, nylons, polypropylenes, polyethylenes, polyethers, polyamides, polyesteramides, polyvinylalcohols, polyhydroxyalkanoates, polysaccharides, and combinations thereof. Further, the synthetic fibers can be a single component (i.e., single synthetic material or mixture makes up entire fiber), bi-component (i.e., the fiber is divided into regions, the regions including two or more different synthetic materials or mixtures thereof and may include co-extruded fibers and core and sheath fibers) and combinations thereof. Bicomponent fibers can be used as a component fiber of the structure, and/or they may be present to act as a binder for the other fibers present in the fibrous structure.

Any or all of the synthetic fibers may be treated before, during, or after manufacture to change any desired properties of the fibers. The substrate may comprise hydrophilic fibers, hydrophobic fibers, or a combination thereof.

The substrate may comprise various percentages of natural and/or synthetic fibers. For example, in some exemplary configurations, the substrate may comprise 100% synthetic fibers. In another exemplary configuration, the substrate may comprise natural and synthetic fibers. For example, the substrate may comprise from about 0% to about 90% natural fibers, with the balance comprising synthetic fibers. The substrate may be comprised of 10%, 20%, 30%, 40%, 50%, 60%, 70%, or 80% natural fibers.

The substrate may include filaments. Filaments are typically considered continuous or substantially continuous in nature. Non-limiting examples of filaments include melt-blown and/or spunbond filaments. Non-limiting examples of materials that can be spun into filaments include natural polymers, such as starch, starch derivatives, cellulose and cellulose derivatives, hemicellulose, hemicellulose derivatives, chitin, chitosan, polyisoprene (cis and trans), peptides, polyhydroxyalkanoates, and synthetic polymers including, but not limited to, thermoplastic polymer filaments comprising thermoplastic polymers, such as polyesters, nylons, polyolefins such as polypropylene filaments, polyethylene filaments, polyvinyl alcohol and polyvinyl alcohol derivatives, sodium polyacrylate (absorbent gel material) filaments, and copolymers of polyolefins such as polyethylene-octene, and biodegradable or compostable thermoplastic fibers such as polylactic acid filaments, polyvinyl alcohol filaments, and polycaprolactone filaments. The filaments may be monocomponent or multicomponent, such as bicomponent filaments.

The substrate may comprise a plurality of filaments, a plurality of solid additives, such as fibers, and a mixture of filaments and solid additives.

In certain configurations, it may be desirable to have particular combinations of fibers to provide desired characteristics. For example, it may be desirable to have fibers of certain lengths, widths, coarseness or other characteristics combined in certain layers, or separate from each other. The fibers may be of virtually any size and may have an average length from about 1 mm to about 60 mm. Average fiber length refers to the length of the individual fibers if straightened out. The fibers may have an average fiber width of greater than about 5 micrometers. The fibers may have an average fiber width of from about 5 micrometers to about 50 micrometers. The fibers may have a coarseness of greater than about 5 mg/100 m. The fibers may have a coarseness of from about 5 mg/100 m to about 75 mg/100 m.

Figure 2:
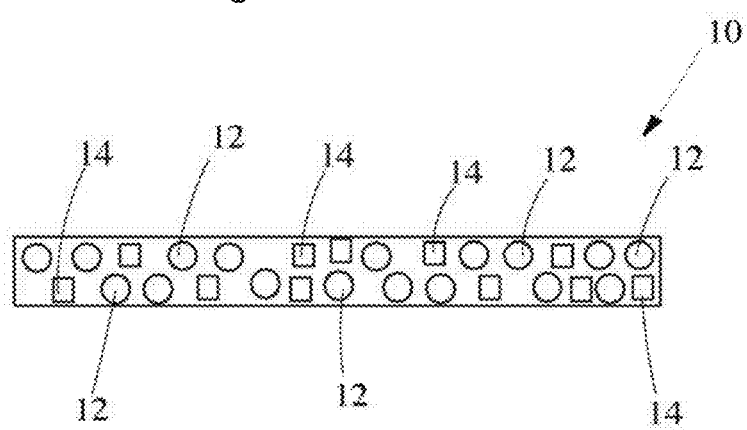
FIG. 2 is a cross-sectional view of the substrate of FIG. 1 taken along line 2-2.

FIGS. 1 and 2 show schematic representations of an example substrate. As shown in FIGS. 1 and 2, the substrate 10 may be a co-formed structure. The substrate 10 comprises a plurality of filaments 12, such as polypropylene filaments, and a plurality of solid additives, such as wood pulp fibers 14. The filaments 12 may be randomly arranged as a result of the process by which they are spun and/or formed into the fibrous structure 10. The wood pulp fibers 14, may be randomly dispersed throughout the fibrous structure 10 in the x-y plane. The wood pulp fibers 14 may be non-randomly dispersed throughout the fibrous structure in the z-direction. In one example (not shown), the wood pulp fibers 14 are present at a higher concentration on one or more of the exterior, x-y plane surfaces than within the fibrous structure along the z-direction.

Figure 3:
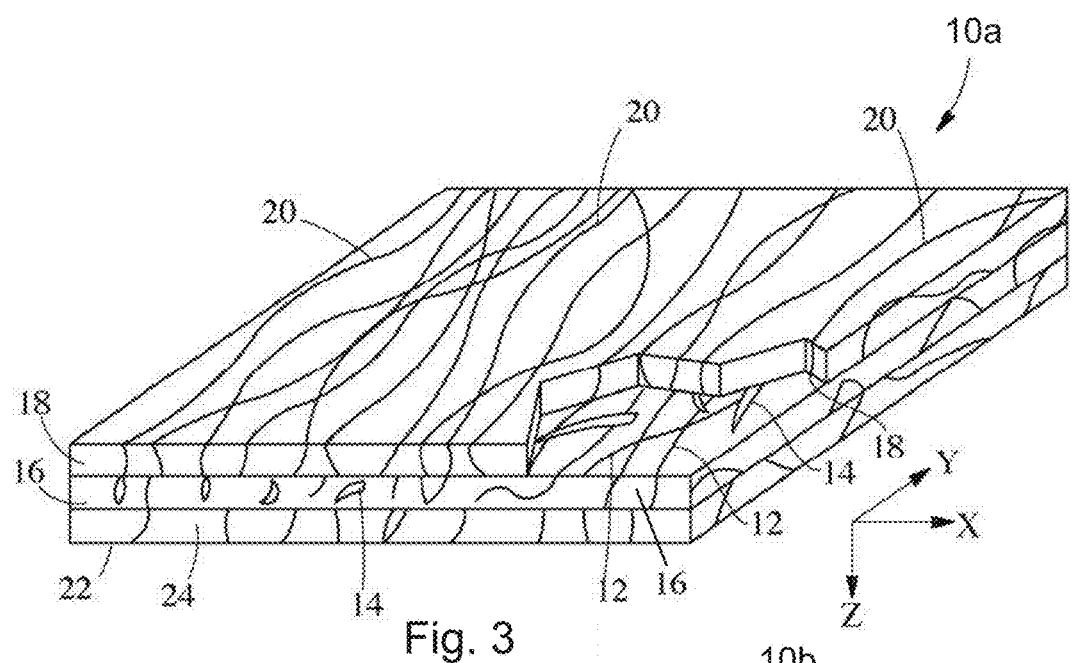
FIG. 3 is a schematic, perspective partially cut-away view of a substrate in accordance with one non-limiting embodiment of the present disclosure.

FIG. 3 shows another exemplary configuration of a layered substrate 10a. The layered substrate 10a comprises a first layer 16 comprising a plurality of filaments 12, such as polypropylene filaments, and a plurality of solid additives, in this example, wood pulp fibers 14. The layered substrate 10a further comprises a second layer 18 comprising a plurality of filaments 20, such as polypropylene filaments. In one example, the first and second layers 16, 18, respectively, are sharply defined zones of concentration of the filaments and/or solid additives. The plurality of filaments 20 may be deposited directly onto a surface of the first layer 16 to form a layered substrate 10a that comprises the first and second layers 16, 18, respectively.

Further, the layered substrate 10a may comprise a third layer 22, as shown in FIG. 3. The third layer 22 may comprise a plurality of filaments 24, which may be the same or different from the filaments 20 and/or 16 in the second 18 and/or first 16 layers. As a result of the addition of the third layer 22, the first layer 16 is positioned, for example sandwiched, between the second layer 18 and the third layer 22. The plurality of filaments 24 may be deposited directly onto a surface of the first layer 16, opposite from the second layer 18, to form the layered substrate 10a that comprises the first, second and third layers 16, 18, 22, respectively.

Figure 4:
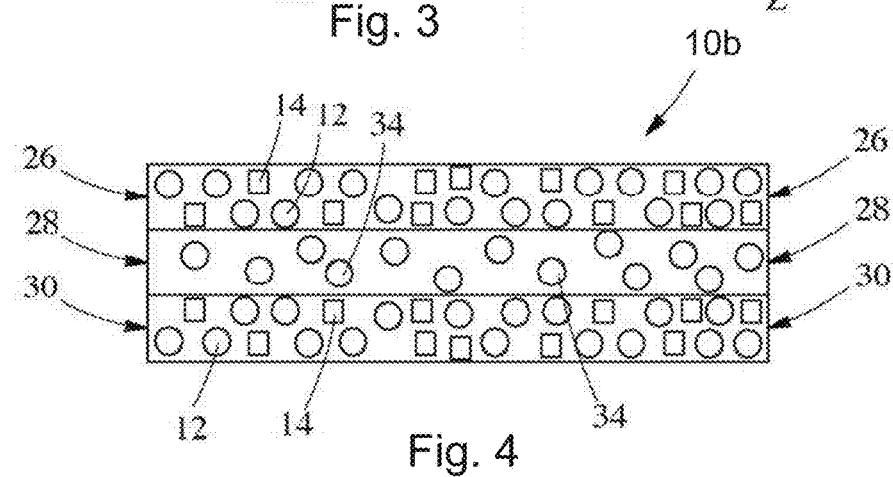
FIG. 4 is a schematic, cross-sectional view of a substrate in accordance with one non-limiting embodiment of the present disclosure.

FIG. 4 shows another exemplary substrate in the form of a layered substrate 10b. The layered substrate 10b comprises a first layer 26, a second layer 28 and optionally a third layer 30. The first layer 26 comprises a plurality of filaments 12, such as polypropylene filaments, and a plurality of solid additives, such as wood pulp fibers 14. The second layer 28 may comprise any suitable filaments, solid additives and/or polymeric films. In one example, the second layer 28 comprises a plurality of filaments 34. In one example, the filaments 34 comprise a polymer selected from the group consisting of: polysaccharides, polysaccharide derivatives, polyvinylalcohol, polyvinylalcohol derivatives and mixtures thereof.

In other exemplary configurations, a substrate may comprise two outer layers consisting of 100%, by total weight, filaments and an inner layer consisting of 100%, by total weight, fibers.

The substrate may comprise any suitable amount of filaments and any suitable amount of solid additives. For example, the substrate may comprise from about 10% to about 70% and/or from about 20% to about 60% and/or from about 30% to about 50% by dry weight of the substrate of filaments and from about 90% to about 30% and/or from about 80% to about 40% and/or from about 70% to about 50% by dry weight of the substrate of solid additives, such as wood pulp fibers. In one example, the substrate comprises filaments.

The filaments and solid additives may be present in substrate according to the present invention at weight ratios of filaments to solid additives of from at least about 1:1 and/or at least about 1:1.5 and/or at least about 1:2 and/or at least about 1:2.5 and/or at least about 1:3 and/or at least about 1:4 and/or at least about 1:5 and/or at least about 1:7 and/or at least about 1:10.

Non-limiting examples of suitable polypropylenes for making the filaments of the present invention are commercially available from Lyondell-Basell and Exxon-Mobil.

Any hydrophobic or non-hydrophilic materials within the substrate, such as polypropylene filaments, may be surface treated and/or melt treated with a hydrophilic modifier. Non-limiting examples of surface treating hydrophilic modifiers include surfactants, such as Triton X-100. Non-limiting examples of melt treating hydrophilic modifiers that are added to the melt, such as the polypropylene melt, prior to spinning filaments, include hydrophilic modifying melt additives such as VW351 and/or S-1416 commercially available from Polyvel, Inc. and Irgasurf commercially available from Ciba. The hydrophilic modifier may be associated with the hydrophobic or non-hydrophilic material at various levels. In one example, the hydrophilic modifier is associated with the hydrophobic or non-hydrophilic material at a level of less than about 20% and/or less than about 15% and/or less than about 10% and/or less than about 5% and/or less than about 3% to about 0% by dry weight of the hydrophobic or non-hydrophilic material.

The substrate may include optional additives, each, when present, at individual levels of from about 0% and/or from about 0.01% and/or from about 0.1% and/or from about 1% and/or from about 2% to about 95% and/or to about 80% and/or to about 50% and/or to about 30% and/or to about 20% by dry weight of the substrate. Non-limiting examples of optional additives include permanent wet strength agents, temporary wet strength agents, dry strength agents such as carboxymethylcellulose and/or starch, softening agents, lint reducing agents, opacity increasing agents, wetting agents, odor absorbing agents, temperature indicating agents, color agents, dyes, osmotic materials, microbial growth detection agents, antibacterial agents and mixtures thereof.

The fibers may be circular in cross-section, dog-bone shape, delta (i.e., triangular cross section), trilobal, ribbon, or other shapes typically produced as staple fibers. Likewise, the fibers can be conjugate fibers such as bicomponent fibers. The fibers may be crimped and may have a finish, such as a lubricant, applied.

The substrate materials may also be treated to improve the softness and texture thereof. The substrate may be subjected to various treatments, such as physical treatment, hydro-molding, hydro-embossing, and ring rolling, as described in U.S. Pat. No. 5,143,679; structural elongation, as described in U.S. Pat. No. 5,518,801; consolidation, as described in U.S. Pat. Nos. 5,914,084; 6,114,263; 6,129,801 and 6,383,431; stretch aperturing, as described in U.S. Pat. Nos. 5,628,097; 5,658,639; and 5,916,661; differential elongation, as described in U.S. Pat. No. 7,037,569, and other solid state formation technologies as described in U.S. Pat. No. 7,553,532 and U.S. Pat. No. 7,410,683; zone activation, and the like; chemical treatment, such as rendering part or all of the substrate hydrophobic, and/or hydrophilic, and the like; thermal treatment, such as thermal-embossing, softening of fibers by heating, thermal bonding and the like; and combinations thereof.

Without wishing to be bound by theory, it is believed that a textured substrate may further enable the ease of removal of soils by improving the ability to grip or otherwise lift the soils from the surface during cleansing. Any one of a number of texture elements may be useful in improving the ability to grip or otherwise lift the soil from the surface during cleansing such as continuous hydro-molded elements, hollow molded element, solid molded elements, circles, squares, rectangles, ovals, ellipses, irregular circles, swirls, curly cues, cross hatches, pebbles, lined circles, linked irregular circles, half circles, wavy lines, bubble lines, puzzles, leaves, outlined leaves, plates, connected circles, changing curves, dots, honeycombs, and the like, and combinations thereof. The texture elements may be hollow elements. The texture elements may be connected to each other. The texture elements may overlap each other.

The substrate may have a basis weight between about 15, 30, 40, or 45 grams/m$^2$ and about 65, 75, 85, 95, or 100 grams/m$^2$. A suitable substrate may be a carded nonwoven comprising a 40/60 blend of viscose fibers and polypropylene fibers having a basis weight of 58 grams/m$^2$ as available from Suominen of Tampere, Finland as FIBRELLA 3160. FIBRELLA 3160 is a 58 grams/m$^2$ nonwoven web comprising 60%, by total weight, of 1.5 denier polypropylene fibers and 40%, by total weight, of 1.5 denier viscose fibers. Another suitable material may be FIBRELLA 3100 which is a 62 grams/m$^2$ nonwoven web comprising 50%, by total weight, of 1.5 denier polypropylene fibers and 50%, by total weight, of 1.5 denier viscose fibers. In both of these commercially available fibrous webs, the average fiber length is about 38 mm. Another suitable material for use as a substrate may be SAWATEX 2642 as available from Sandler AG of Schwarzenbach/Salle, Germany. Yet another suitable material for use as a substrate may have a basis weight of from about 50 grams/m$^2$ to about 60 grams/m$^2$ and have a 20/80 blend of viscose fibers and polypropylene fibers. The substrate may also be a 60/40 blend of pulp and viscose fibers. Exemplary nonwoven substrates are described in U.S. Patent Publication 2012/066852 and U.S. Patent Publication 2011/244199.

In some configurations, the surface of the substrate may be essentially flat. In other configurations, the surface of the substrate may optionally contain raised and/or lowered portions. The raised and/or lowered portions can be in the form of logos, indicia, trademarks, geometric patterns, and/or images of the surfaces that the substrate is intended to clean (i.e., infant's body, face, etc.). The raised and/or lowered portions may be randomly arranged on the surface of the substrate or be in a repetitive pattern of some form.

The substrate may be biodegradable. For example, the substrate could be made from a biodegradable material such as a polyesteramide, or high wet strength cellulose. In some exemplary configurations, the substrate may be dispersible.

The substrate may further comprise prints, which may provide aesthetic appeal. Non-limiting examples of prints include figures, patterns, letters, pictures and combinations thereof.

Package

Absorbent articles of the present disclosure may be packaged in a container. A first absorbent article having a first functional lotion composition may be packaged in a first container and a second absorbent article having a second functional lotion composition may be packaged in a second container, wherein the first functional lotion composition is different from the second functional lotion composition. More specifically, the first functional lotion composition may include a first fragrance accord and a first lotion formula, which appeals to light experience seeking consumers, and the second functional lotion composition may include a second fragrance accord and a second lotion formula, which appeals to heavy experience seeking consumers. The first and second containers may be simultaneously available for retail purchase. The first and second absorbent articles may be commonly-branded and/or commonly-sourced.

Further, the first container and the second container may be structurally similar. For example, the first container and the second container may be similarly sized and/or similarly proportioned. In some exemplary embodiments, the first container and the second container may have the same dispensing mechanism and/or be made from the same material.

Array of Absorbent Articles

In some example embodiments, an array of at least two products may include a first absorbent article, such as a first wipe, and a second absorbent article, such as a second wipe. The first absorbent article may include a first supply of absorbent articles formed from a first substrate. The first absorbent article may be moistened with a first functional lotion composition directed at light experience seeking consumers. The first functional lotion composition may include a first fragrance accord and a first lotion formula. The second absorbent article may be formed from a second substrate and moistened with a second functional lotion composition directed at heavy experience seeking consumers. The second functional lotion composition may include a second fragrance accord and a second lotion formula. The first functional lotion composition may differ from the second functional lotion composition. For example, the formula of the first lotion composition may differ from the formula of the second lotion composition. Further, the first fragrance accord of the first functional lotion composition may differ from the second fragrance accord of the second functional lotion composition.

The second fragrance accord may differ from the first fragrance accord in that the second fragrance accord may include a disproportionate amount of at least one of top notes, middle notes, and base notes than the first fragrance accord. For example, in some embodiments, the second fragrance accord may include a greater amount of base notes than the first fragrance accord. In some other embodiments, the second fragrance accord may include a greater proportion of base notes than the first fragrance accord and the first fragrance accord may include a greater proportion of middle notes than the second fragrance accord.

Additionally, the second functional lotion composition may differ from the first functional lotion composition in at least one of peak viscosity and average peak dynamic frictional force. In some embodiments, for example, the first lotion formula may have a peak viscosity that is less than the peak viscosity of the second lotion formula. In some embodiments, the first lotion formula may also have an average peak dynamic frictional force that is greater than an average peak dynamic frictional force of the second lotion formula.

More specifically, in some example embodiments, an array of at least two products may include a first absorbent article and a second absorbent article. The first absorbent article may include a first fragrance accord and may have at least one of a first peak viscosity and a first average peak dynamic frictional force, which is to appeal to light experience seeking consumers. The first fragrance accord may include from about 10% to about 15%, by total weight of the accord, of a perfume raw material having a vapor pressure of greater than 0.08 Torr at 25° C.; from about 35% to about 65%, by total weight of the accord, of a perfume raw material having a vapor pressure from 0.006 Torr at 25° C. to 0.08 Torr at 25° C.; and from about 20% to about 30%, by total weight of the accord, of a perfume raw material having a vapor pressure of less than 0.006 Torr at 25° C. The first peak viscosity may be less than about 60 mPa·s. The first average peak dynamic frictional force may be greater than about 25 g. Further, the second absorbent article may include a second fragrance accord and have at least one of a second peak viscosity and a second average peak dynamic frictional force, which is to appeal to heavy experience seeking consumers. The second fragrance accord may include from about 10% to about 20%, by total weight of the accord, of a perfume raw material having a vapor pressure of greater than 0.08 Torr at 25° C.; from about 20% to about 30%, by total weight of the accord, of a perfume raw material having a vapor pressure from 0.006 Torr at 25° C. to 0.08 Torr at 25° C.; and from about 45% to about 70%, by total weight of the accord, of a perfume raw material having a vapor pressure of less than 0.006 Torr at 25° C. The second peak viscosity may be greater than about 75 mPa·s. The second average peak dynamic frictional force may be less than about 25 g.

In some example embodiments, an array of at least two commonly-branded but differentiated products may include a first absorbent article and a second absorbent article. The first absorbent article may include a first fragrance accord and may have at least one of a first peak viscosity and a first average peak dynamic frictional force, which is to appeal to light experience seeking consumers. The first fragrance accord may include from about 10% to about 15%, by total weight of the accord, of a perfume raw material having a Kovats Index of less than 1300; from about 35% to about 65%, by total weight of the accord, of a perfume raw material having a Kovats Index from 1300 to 1450; and from about 20% to about 30%, by total weight of the accord, of a perfume raw material having a Kovats Index of greater than 1450. The first peak viscosity may be less than about 60 mPa·s. The first average peak dynamic frictional force may be greater than about 50 g. Further, the second absorbent article may include a second fragrance accord and have at least one of a second peak viscosity and a second average peak dynamic frictional force, which is to appeal to heavy experience seeking consumers. The second fragrance accord may include from about 10% to about 20%, by total weight of the accord, of a perfume raw material having a Kovats Index of less than 1300; from about 20% to about 30%, by total weight of the accord, of a perfume raw material having a Kovats Index from 1300 to 1450; and from about 45% to about 70%, by total weight of the accord, of a perfume raw material having a Kovats Index of greater than 1450. The second peak viscosity may be greater than about 80 mPa·s. The second average peak dynamic frictional force may be less than about 50 g.

EXAMPLES

Fragrance Accord

Example 1, shown in Table 1, is an illustrative, non-limiting formula of a fragrance accord of the present disclosure. The fragrance accord shown in Table 1 may be appealing to light experience seeking consumers.

TABLE 1

| Perfume Raw Material Name | Weight % | Vapor Pressure at 25° C. (Torr) | Kovats Index |
|---|---|---|---|
| Prenyl Acetate | 0.20% | 4.170 | 931.3 |
| Linalool | 5.00% | 0.083 | 1159 |
| Benzyl Acetate | 4.00% | 0.187 | 1197.3 |
| Methyl Nonyl Ketone | 1.00% | 0.112 | 1297.4 |
| Iso Nonyl Acetate | 0.70% | 0.382 | 1294.4 |
| Dihydro Myrcenol | 4.00% | 0.124 | 1103.8 |
| Total Top Notes | 14.90% | | |
| Undecyl Aldehyde | 0.10% | 0.061 | 1311.6 |
| 4-Tertiary Butyl Cyclohexyl Acetate | 15.30% | 0.069 | 1351.5 |
| Eugenol | 20.00% | 0.009 | 1436.7 |
| Mayol | 20.00% | 0.011 | 1235.6 |
| Total Middle Notes | 55.40% | | |
| Hexyl Cinnamic Aldehyde | 5.00% | 0.001 | 1797.9 |
| Benzophenone | 2.00% | 0.001 | 1662 |
| Ethylene Brassylate | 3.00% | 0.000 | 1931 |
| Methyl Cedrylone | 2.00% | 0.001 | 1828.3 |
| Methyl Dihydro Jasmonate | 10.00% | 0.001 | 1550.9 |
| Lyral | 2.70% | 8.57%-05 | 1587 |
| Benzyl Salicylate | 5.00% | 0.000 | 1920.3 |

TABLE 1-continued

| Perfume Raw Material Name | Weight % | Vapor Pressure at 25° C. (Torr) | Kovats Index |
|---|---|---|---|
| Total Base Notes | 29.70% | | |
| TOTAL | 100.00% | | |

Example 2, shown in Table 2, is an illustrative, non-limiting formula of a fragrance accord of the present disclosure. The fragrance accord shown in Table 2 may be appealing to heavy experience seeking consumers.

TABLE 2

| Perfume Raw Material Name | Weight % | Vapor Pressure at 25° C. (Torr) | Kovats Index |
|---|---|---|---|
| Prenyl Acetate | 1.00% | 4.170 | 931.3 |
| Linalool | 5.00% | 0.083 | 1159 |
| Benzyl Acetate | 4.00% | 0.187 | 1197.3 |
| Methyl Nonyl Ketone | 1.00% | 0.112 | 1297.4 |
| Iso Nonyl Acetate | 0.70% | 0.382 | 1294.4 |
| Dihydro Myrcenol | 8.00% | 0.124 | 1103.8 |
| Total Top Notes | 19.70% | | |
| Undecyl Aldehyde | 0.20% | 0.061 | 1311.6 |
| 4-Tertiary Butyl Cyclohexyl Acetate | 5.00% | 0.069 | 1351.5 |
| Eugenol | 10.00% | 0.009 | 1436.7 |
| Mayol | 5.00% | 0.011 | 1235.6 |
| Total Middle Notes | 20.20% | | |
| Hexyl Cinnamic Aldehyde | 15.00% | 0.001 | 1797.9 |
| Benzophenone | 2.00% | 0.001 | 1662 |
| Ethylene Brassylate | 10.10% | 0.000 | 1931 |
| Methyl Cedrylone | 5.00% | 0.001 | 1828.3 |
| Methyl Dihydro Jasmonate | 20.00% | 0.001 | 1550.9 |
| Lyral | 3.00% | 8.57%-05 | 1587 |
| Benzyl Salicylate | 5.00% | 0.000 | 1920.3 |
| Total Base Notes | 60.10% | | |
| TOTAL | 100.00% | | |

Example 3, shown in Table 3, is an illustrative, non-limiting formula of a fragrance accord of the present disclosure. The fragrance accord shown in Table 3 may be appealing to heavy experience seeking consumers.

TABLE 3

| Perfume Raw Material Name | Weight % | Vapor Pressure at 25° C. (Torr) | Kovats Index |
|---|---|---|---|
| Prenyl Acetate | 3.00% | 4.170 | 931.3 |
| Linalool | 15.90% | 0.083 | 1159 |
| Benzyl Acetate | 15.00% | 0.187 | 1197.3 |
| Methyl Nonyl Ketone | 1.00% | 0.112 | 1297.4 |
| Iso Nonyl Acetate | 5.00% | 0.382 | 1294.4 |
| Dihydro Myrcenol | 20.00% | 0.124 | 1103.8 |
| Total Top Notes | 59.90% | | |
| Undecyl Aldehyde | 0.10% | 0.061 | 1311.6 |
| 4-Tertiary Butyl Cyclohexyl Acetate | 3.00% | 0.069 | 1351.5 |
| Eugenol | 3.00% | 0.009 | 1436.7 |
| Mayol | 5.00% | 0.011 | 1235.6 |
| Total Middle Notes | 11.10% | | |
| Hexyl Cinnamic Aldehyde | 5.00% | 0.001 | 1797.9 |
| Benzophenone | 1.00% | 0.001 | 1662 |
| Ethylene Brassylate | 3.00% | 0.000 | 1931 |

TABLE 3-continued

| Perfume Raw Material Name | Weight % | Vapor Pressure at 25° C. (Torr) | Kovats Index |
|---|---|---|---|
| Methyl Cedrylone | 2.00% | 0.001 | 1828.3 |
| Methyl Dihydro Jasmonate | 10.00% | 0.001 | 1550.9 |
| Lyral | 3.00% | 8.57%-05 | 1587 |
| Benzyl Salicylate | 5.00% | 0.000 | 1920.3 |
| Total Base Notes | 29.00% | | |
| TOTAL | 100.00% | | |

Lotion Formula

Examples 4-6, shown in Tables 4 through 6, respectively, are illustrative, non-limiting lotion formulas of the present disclosure. Examples 4-6 may appeal to light experience seeking consumers.

TABLE 4

| Example 4 - Ingredient Name | W/W (%) |
|---|---|
| Water | Q.S. |
| Disodium EDTA | 0.10 |
| Sodium Benzoate | 0.18 |
| Xanthan Gum* | 0.06 |
| PEG-40 Hydrogenated Castor Oil | 0.44 |
| BIS-PEG/PPG-16/16 PEG/PPG-16/16 Dimethicone Caprylic Capric Triglyceride† | 0.10 |
| Preservative Enhancing Agent□ | 0.20 |
| Citric Acid | 0.56 |
| Trisodium Citrate | 0.30 |
| Perfume | 0.00 |

TABLE 5

| Example 5 - Ingredient Name | W/W (%) |
|---|---|
| Water | Q.S. |
| Disodium EDTA | 0.10 |
| Sodium Benzoate | 0.24 |
| Xanthan Gum* | 0.06 |
| PEG-40 Hydrogenated Castor Oil | 0.44 |
| BIS-PEG/PPG-16/16 PEG/PPG-16/16 Dimethicone Caprylic Capric Triglyceride† | 0.10 |
| Preservative Enhancing Agent□ | 0.30 |
| Citric Acid | 0.56 |
| Trisodium Citrate | 0.30 |
| Perfume | 0.07 |

TABLE 6

| Example 6 - Ingredient Name | W/W (%) |
|---|---|
| Water | Q.S. |
| Disodium EDTA | 0.10 |
| Sodium Benzoate | 0.18 |
| Xanthan Gum* | 0.04 |
| PEG-40 Hydrogenated Castor Oil | 0.44 |
| BIS-PEG/PPG-16/16 PEG/PPG-16/16 Dimethicone Caprylic Capric Triglyceride† | 0.10 |
| Preservative Enhancing Agent□ | 0.20 |
| Citric Acid | 0.56 |
| Trisodium Citrate | 0.30 |
| Pentadecalactone⊖ | 0.05 |

Examples 7 and 8, as shown in Tables 7 and 8, respectively, are illustrative, non-limiting lotion formulas of the present disclosure. Examples 7 and 8 may appeal to heavy experience seeking consumers.

TABLE 7

| Example 7 - Ingredient Name | W/W (%) |
|---|---|
| Water | Q.S. |
| Disodium EDTA | 0.10 |
| Sodium Benzoate | 0.12 |
| Xanthan Gum* | 0.18 |
| PEG-40 Hydrogenated Castor Oil | 0.44 |
| BIS-PEG/PPG-16/16 PEG/PPG-16/16 Dimethicone Caprylic Capric Triglyceride† | 0.10 |
| Phenoxyethanol/Ethylhexylglycerin° | 0.30 |
| Benzyl Alcohol | 0.30 |
| Citric Acid | 0.53 |
| Trisodium Citrate | 0.33 |
| Perfume | 0.07 |

TABLE 8

| Example 8 - Ingredient Name | W/W (%) |
|---|---|
| Water | Q.S. |
| Disodium EDTA | 0.10 |
| Sodium Benzoate | 0.12 |
| Xanthan Gum* | 0.18 |
| PEG-40 Hydrogenated Castor Oil | 0.44 |
| BIS-PEG/PPG-16/16 PEG/PPG-16/16 Dimethicone Caprylic Capric Triglyceride† | 0.45 |
| Phenoxyethanol/Ethylhexylglycerin° | 0.30 |
| Benzyl Alcohol | 0.30 |
| Citric Acid | 0.53 |
| Trisodium Citrate | 0.33 |
| Perfume | 0.14 |

Examples 9, 10, and 11, shown in Tables 9, 10, and 11, respectively, are illustrative, non-limiting lotion formula of the present disclosure. Examples 9, 10, and 11 may appeal to heavy experience seeking consumers.

TABLE 9

| Example 9 - Ingredient Name | W/W (%) |
|---|---|
| Water | Q.S. |
| Disodium EDTA | 0.10 |
| Sodium Benzoate | 0.12 |
| Trisodium Citrate | 0.33 |
| Xanthan Gum* | 0.15 |
| Montmorilonite Clay‡ | 0.27 |
| Sodium Stearate⁻ | 0.27 |
| Glyceryl Stearate Citrate^Δ | 0.27 |
| Phenoxyethanol Ethylhexylglycerine° | 0.30 |
| Benzyl Alcohol | 0.30 |
| Sunflower Seed Oil◠ | 2.50 |
| Citric Acid | 0.65 |

TABLE 10

| Example 10 - Ingredient Name | W/W (%) |
|---|---|
| Water | Q.S. |
| Disodium EDTA | 0.10 |
| Sodium Benzoate | 0.12 |
| Trisodium Citrate | 0.33 |
| Xanthan Gum* | 0.15 |
| Montmorilonite Clays‡ | 0.27 |
| Sodium Stearate⁻ | 0.27 |
| Glyceryl Stearate Citrate^Δ | 0.27 |
| Preservative Enhancing Agent□ | 0.20 |
| Sunflower Seed Oil◠ | 2.50 |
| Citric Acid | 0.65 |

TABLE 11

| Example 11 - Ingredient Name | W/W (%) |
|---|---|
| Water | Q.S. |
| Disodium EDTA | 0.10 |
| Sodium Benzoate | 0.18 |
| Trisodium Citrate | 0.30 |
| Polyoxyethylene (20) stearyl ether≪ | 0.40 |
| Stearyl Alcohol˚ | 1.00 |
| Polyoxyethylene (2) stearyl ether^Φ | 0.70 |
| Preservative Enhancing Agent□ | 0.20 |
| Sunflower Seed Oil◠ | 5.00 |
| Citric Acid | 0.48 |

*Xanthan FG as supplied by Jungbunzlauer, Austria
†Abil Care 85 as supplied by Evonik Goldschmidt Corp, Hopewell, Va.
□Sorbitan caprylate or glyceryl caprylate/caprate as supplied by Clariant under the designation VELSAN® SC, by Peter Cremer under the designation CremerCOOR® GC810, CremerCOOR® GCB, or IMWITOR® 742, or by Abitec under the designation CAPMUL® 708G
ΩExaltolide as supplied by Firmenich, Plainsboro, N.J.
‡Mineral Colloid BP from Southern Clay Products of Austin, Tex.
⁻OP-100V from Hallstar Company of Chicago, Ill.
°EUXYL® PE 9010, available from Schulke & Mayr GmbH of Germany
◠High Oleic Sunflower Seed Oil, available from Cargill of Minneapolis, Minn.
≪Brij S20-PA-(MH) as supplied by Croda Inc. of Edison, N.J.
˚CO-1897 as supplied by Peter Cremer of Cincinnati, Ohio
ΦBrij 52-SO-(MH) as supplied by Croda Inc. of Edison, N.J.

Test Methods

Kovats Index Method

Kovats Index is determined by gas chromatography. An Agilent Technologies 6890 gas chromatogram equipped with a DB-5 column and a Flame Ionization Detector (FID), or equivalent instrument with FID, is used. A suitable column is 30 m×0.25 mm i.d., with a 0.25 um film. The carrier gas is helium. Gas flow rate, injection temperature and column temperature are adjusted to achieve good separation of peaks. For example; helium flow rate from 1 to 3 mL/min; inlet temperature 280° C.; column temperature start at 40° C., ramp to 90° C. at 25° C./min, then ramp to 170° C. at 15° C./min, then hold at 170° C. for 2 min. Different conditions may be required depending on the nature of the column and analytes.

A linear alkane hydrocarbon standard mix (C8-C22) available from Aldrich Co., AccuStandard Co., or equivalent is injected and the retention time for each component is noted. The test sample (appropriately diluted in a suitable solvent) is injected under the same conditions, and the retention time for each component is noted as well as the area under each peak. The retention time for each peak in the test sample will lie between the retention times of two alkanes in the standard mix.

Kovats Index I is calculated for each component in the test sample using the equation:

$$I = 100 \times \left[ n + (N - n) \frac{\log(t'_{r(unknown)}) - \log(t'_{r(n)})}{\log(t'_{r(N)}) - \log(t'_{r(n)})} \right]$$

Where I is the Kovats Index, n is the number of carbon atoms in the smaller alkane whose peak is adjacent to that of the test component, N is the number of carbon atoms in the larger alkane whose peak is adjacent to that of the test component, $t'_r$ is the retention time.

The FID Area Fraction ($AF_i$) is determined for each component in the test sample as a fraction of the total integrated peak area for all components in the test sample. The FID Area Fraction of each component is taken as the mass fraction of that component in the test sample.

Peak Complex Viscosity Test Method

This method is suitable for determination of peak viscosity, also referred to herein as peak complex viscosity, of a liquid composition. A Haake Rheostress 600 rotational rheometer available from Thermo Fisher Scientific of Waltham, Mass. or equivalent instrument is used. A 60 mm diameter parallel plate fixture is used and the temperature of the specimen is controlled to 25±1° C. during the viscosity measurement by means of a suitable circulating water bath.

The instrument is programmed to run in Amplitude Sweep mode at a frequency of 0.16 Hz starting at a shear stress Tau=0.05 Pa and ending at Tau=25.6 Pa with a maximum measurement time of 300 seconds. The amplitude is increased in 10 steps on a linear scale using the following Tau values:

| Step | Tau [Pa] |
|---|---|
| 1 | 0.05 |
| 2 | 0.10 |
| 3 | 0.20 |
| 4 | 0.40 |
| 5 | 0.80 |
| 6 | 1.60 |
| 7 | 3.20 |
| 8 | 6.40 |
| 9 | 12.80 |
| 10 | 25.60 |

The instrument is calibrated for inertia and zero gap according to the procedures specified by the instrument manufacturer. The plates are separated and cleaned with a suitable solvent and allowed to dry. A sufficient quantity of the liquid composition is deposited onto the center of the base plate using a suitable pipette or equivalent to ensure that the liquid composition will completely fill the gap when the plates are brought together. Typically this is approximately 2.5 ml of the lotion composition. The gap is then closed to 0.800 mm and the sample is trimmed by running a rubber policeman or equivalent around the periphery of the plates to remove any excess liquid. The test is then initiated and the relevant data (complex viscosity Eta* as a function of shear stress Tau) are acquired.

The Peak Complex Viscosity is the highest recorded value for Eta*. This value can be obtained directly from the raw data.

Multi-Cycle Dynamic Friction Force Method

The Multi-Cycle Dynamic Friction Force test method is performed on a constant rate of extension tensile tester with computer interface (MTS Criterion Model 42 using TestWorks™ 4.1 Software, as available from MTS Systems Corp., Eden Prairie, Minn. or equivalent). For these experiments the tensile tester is mounted on its back, so that its pull axis is horizontal. This configuration requires a special load cell designed to resist the horizontal component from the downward force of any attached fixture. A suitable load cell is a 10N load cell Model LSB-101 also available from MTS or equivalent. All testing is performed in a room maintained at 23° C.±2° C. and 50%±2% relative humidity, and all samples and materials are conditioned at 23° C.±2° C. and 50%±2% relative humidity for 24 hours prior to testing.

Figure 6:
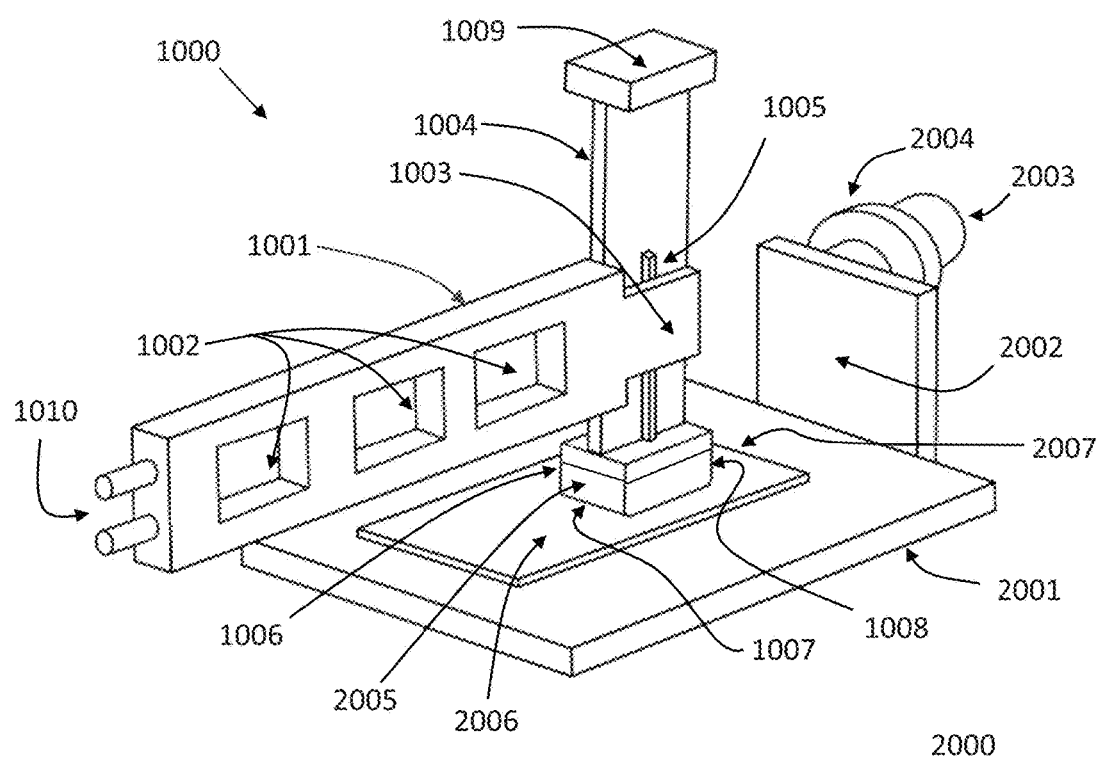
FIG. 6 is a schematic, perspective view of a fixture used in determining the average peak dynamic frictional force for various lotion formulas.

Referring to FIG. 6, two custom fixtures are used: a foot assembly 1000 attached to the movable arm and a platform 2000 attached to the stationary mount of the tensile tester. The foot assembly consists of a horizontal brace 1001 that is 160 mm long by 13 mm wide by 30 mm high made of Delrin material from which cutouts 1002 have been removed to reduce the overall weight of the brace. The brace has an integrated extension 1003 that is 20 mm long by 4 mm wide by 13 mm high from which an aluminum, I-shaped beam 1004 is attached via a low-friction linear slide 1005 (www.mcmaster.com; Part No. 8381K39). The I-beam should be able to freely float vertically. An aluminum foot 1006 that is 20 mm long by 15 mm wide by 5 mm high is attached to the bottom of the beam. The leading 1007 and distil 1008 edges of the foot are rounded to a radius of 2.5 mm. A weight 1009 is attached to the top of the beam to adjust the mass to deliver a pressure of 0.96 KPa by the foot. The foot assembly is mounted to the force gauge with an appropriate connector 1011.

The platform 2000 consists of an aluminum base plate 2001 that is approximately 15 cm long by 10 mm wide and 20 mm thick. The base plate has a perpendicular riser 2002 that holds the base plate parallel to the foot assembly with the bottom of the foot 1006 orthogonal to the base plate's surface. The riser's height dimension is adjusted such that during use the foot 1006 rests on the base plate 2001 and the I-beam may freely move vertically on its linear slide. The platform 2000 is attached to the tensile tester via an instrument appropriate shaft 2003 with a locking collar 2004 that maintains the fixture's alignment.

Program the tensile tester to move the crosshead away from the stationary fixture at 10 mm/sec for 60 mm and then immediately return 60 mm at the same rate. This cycle is repeated 120 times. Force and displacement data is recorded for all cycles at 100 Hz.

Coffi™ collagen (available from Global Packaging Co., Inc. Carlstadt, N.J.) is used as the test substrate for use on both the foot and base plate surfaces. A laminate is formed by adhering the smooth side of the collagen to two-sided tape (available as Coated Tape 592 from Intertape Polymer Group, or equivalent). A rectangular piece of laminate 26 mm by 20 mm is cut for use on the foot 1006 and a second rectangular piece of laminate 26 mm by 102 mm is cut for use on the base plate 2001. Inspect laminates to assure the collagen surface is wrinkle free. Laminates are prepared prior to testing and conditioned at 23° C.±2° C. and 50%±2% relative humidity for 24 hours prior to use.

Remove the protective backing from one of the 26 mm by 20 mm piece of laminate and completely cover the bottom surface of the foot 1006 wrapping excess laminate onto the sides of the foot. Remove the protective backing from one of the 26 mm by 102 mm piece of laminate and adhere it, centered longitudinal and laterally, on the base plate 2001.

Move the crosshead of the tensile tester to place the distal edge of the foot 1008 approximately 10 mm from the distal edge 2007 of the collagen laminate. Zero the crosshead and load cell of the tensile tester. Use a micro pipette to deposit a 30 µL±2 µL drop of test lotion at the leading edge 1007 of the sled. Immediately after depositing the lotion, start the test. After each test the collagen laminate is removed from both the foot and base plate and replaced prior to the next test.

Figure 7:
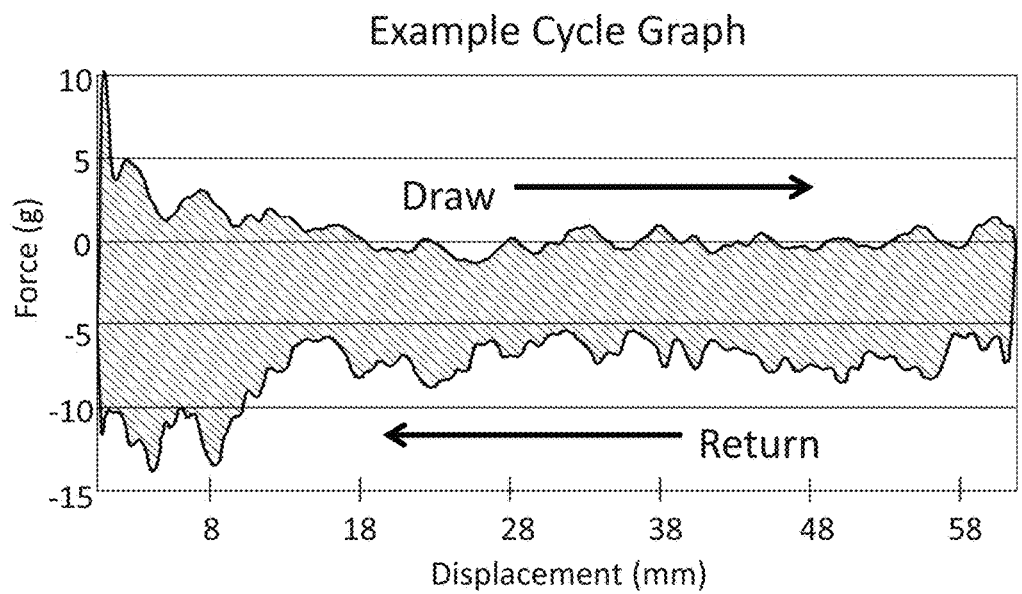
FIG. 7 is a plot of force vs. displacement for an exemplary measurement cycle.
Figure 8:
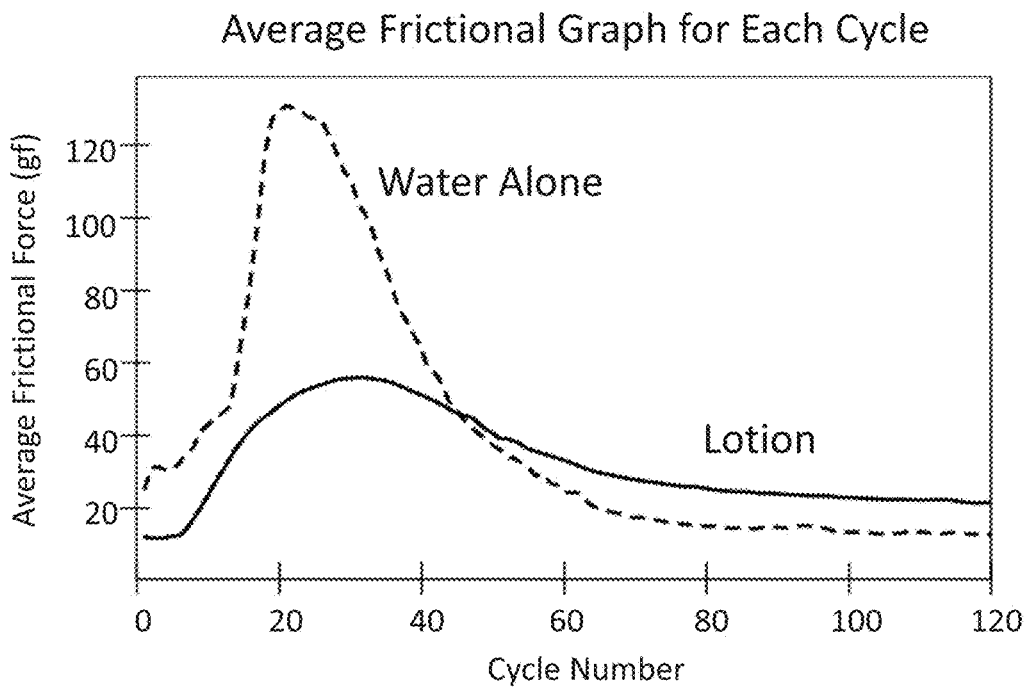
FIG. 8 is a plot of average frictional force vs. cycle number for an exemplary measurement cycle.

From the resulting force verses displacement curves calculate the area under the curve for both the forward and return curves and report to the nearest gf/mm for each of the 120 cycles, as illustrated, for example, in FIGS. 7 and 8. Next, divide the area calculated for each cycle by the total distance traveled (i.e. both draw and return) and report as the Average Frictional Force to the nearest 0.1 gf for each of the 120 cycles. The maximum Average Frictional Force of all cycles can be determined from a histogram of average forces from all cycles. The maximum Average Friction Force is referred to herein as the average peak dynamic frictional force.

Basis Weight Test Method

Basis weight is measured prior to the application of any end-use lotion, cleaning solution, or other liquid composition, etc. to the fibrous structure or wipe, and follows a modified EDANA 40.3-90 (February 1996) method as described herein below.

1. Cut at least three test pieces of the fibrous structure or wipe to specific known dimensions, preferably using a pre-cut metal die and die press. Each test piece typically has an area of at least 0.01 m$^2$.
2. Use a balance to determine the mass of each test piece in grams; calculate basis weight (mass per unit area), in grams per square meter (gsm), using equation (1).

$$\text{Basis Weight} = \frac{\text{Mass of Test Piece(g)}}{\text{Area of Test Piece(m}^2\text{)}} \quad (1)$$

3. For a fibrous structure or wipe sample, report the numerical average basis weight for all test pieces.
4. If only a limited amount of the fibrous structure or wipe is available, basis weight may be measured and reported as the basis weight of one test piece, the largest rectangle possible.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An array of at least two commonly-branded wipes products comprising a first wipes product and a second wipes product, wherein:
the first wipes product comprises:
   a first supply of wipes formed from a first substrate, the first supply of wipes being moistened with a first functional lotion composition, the first functional lotion composition comprising:
      a first fragrance accord; and
      a first lotion formula;
the second wipes product comprises:
   a second supply of wipes formed from a second substrate, the second supply of wipes being moistened with a second functional lotion composition, the second functional lotion composition comprising:
      a second fragrance accord; and
      a second lotion formula;
wherein the second fragrance accord is different from the first fragrance accord, and the second lotion formula is different from the first lotion formula,
wherein the first lotion formula has a first peak viscosity and the second lotion formula has a second peak viscosity, and the first peak viscosity is less than the second peak viscosity;
wherein the first functional lotion composition comprises at least 98.06 wt. % water;
wherein the first functional lotion composition has a peak viscosity from about 5 mPa·s to about 65 mPa·s and an average peak dynamic frictional force from about 25 g to about 60 g;
wherein the second functional lotion composition has a peak viscosity greater than about 75 mPa·s and an average peak dynamic frictional force from about 2.5 g to about 25 g; and
wherein the first functional lotion composition comprises less than 0.3 wt. % sodium benzoate.

2. The array of claim 1, wherein:
the first fragrance accord comprises:
from about 10% to about 15%, by total weight, of a perfume raw material having a vapor pressure of greater than 0.08 Torr at 25° C.;
from about 35% to about 65%, by total weight, of a perfume raw material having a vapor pressure from 0.006 Torr at 25° C. to 0.08 Torr at 25° C.;
from about 20% to about 30%, by total weight, of a perfume raw material having a vapor pressure of less than 0.006 Torr at 25° C.; and
the second fragrance accord comprises:
from about 10% to about 20%, by total weight, of a perfume raw material having a vapor pressure of greater than 0.08 Torr at 25° C.;
from about 20% to about 30%, by total weight, of a perfume raw material having a vapor pressure from 0.006 Torr at 25° C. to 0.08 Torr at 25° C.; and
from about 45% to about 70%, by total weight, of a perfume raw material having a vapor pressure of less than 0.006 Torr at 25° C.

3. The array of claim 1, wherein:
the first fragrance accord comprises:
from about 10% to about 15%, by total weight, of a perfume raw material having a Kovats Index of less than 1300;
from about 35% to about 65%, by total weight, of a perfume raw material having a Kovats Index from 1300 to 1450;
from about 20% to about 30%, by total weight, of a perfume raw material having a Kovats Index of greater than 1450; and
the second fragrance accord comprises:

from about 10% to about 20%, by total weight, of a perfume raw material having a Kovats Index of less than 1300;

from about 20% to about 30%, by total weight, of a perfume raw material having a Kovats Index from 1300 to 1450; and from about 45% to about 70%, by total weight, of a perfume raw material having a Kovats Index of greater than 1450.

4. The array of claim 1, wherein the first substrate and the second substrate each comprises a non-woven material.

5. The array of claim 1, wherein each of the first fragrance accord and the second fragrance accord is neat.

6. The array of claim 1, wherein at least one of the first functional lotion composition and the second functional lotion composition further comprises an emollient.

7. The array of claim 6, wherein the emollient comprises an oil material.

8. The array of claim 1, wherein at least one of the first substrate and the second substrate comprises a co-form structure.

9. The array of claim 1, wherein at least one of the first substrate and the second substrate comprises two or more layers.

10. The array of claim 1, wherein the second substrate has a greater basis weight than the first substrate.

* * * * *